US009567591B2

(12) United States Patent
Lin et al.

(10) Patent No.: US 9,567,591 B2
(45) Date of Patent: Feb. 14, 2017

(54) GENERATION OF HUMAN EMBRYONIC STEM-LIKE CELLS USING INTRONIC RNA

(75) Inventors: Shi-Lung Lin, Arcadia, CA (US);
Shao-Yao Ying, San Marino, CA (US);
David Ts Wu, Taipei (TW)

(73) Assignees: MELLO BIOTECHNOLOGY, INC., Santa Fe Springs, CA (US);
UNIVERSITY OF SOUTHERN CALIFORNIA, Los Angeles, CA (US)

( * ) Notice: Subject to any disclaimer, the term of this patent is extended or adjusted under 35 U.S.C. 154(b) by 1122 days.

(21) Appl. No.: 12/149,725

(22) Filed: May 7, 2008

(65) Prior Publication Data

US 2008/0293143 A1   Nov. 27, 2008

Related U.S. Application Data

(63) Continuation-in-part of application No. 10/439,262, filed on May 15, 2003, and a continuation-in-part of application No. 11/278,143, filed on Mar. 31, 2006.

(60) Provisional application No. 61/000,797, filed on Oct. 29, 2007, provisional application No. 61/007,867, filed on Dec. 17, 2007, provisional application No. 61/006,179, filed on Dec. 28, 2007.

(51) Int. Cl.
| | | |
|---|---|---|
| *C12N 15/11* | (2006.01) | |
| *C07H 21/02* | (2006.01) | |
| *C07H 21/04* | (2006.01) | |
| *C12Q 1/68* | (2006.01) | |
| *C12N 5/02* | (2006.01) | |
| *C12N 15/64* | (2006.01) | |
| *C12N 15/63* | (2006.01) | |

(52) U.S. Cl.
CPC ..................... *C12N 15/63* (2013.01)

(58) Field of Classification Search
None
See application file for complete search history.

(56) References Cited

U.S. PATENT DOCUMENTS

| | | | |
|---|---|---|---|
| 5,843,780 | A | 12/1998 | Thomson |
| 6,090,622 | A | 7/2000 | Gearhart et al. |
| 6,200,806 | B1 | 3/2001 | Thomson |
| 6,245,566 | B1 | 6/2001 | Gearhart et al. |
| 6,331,406 | B1 | 12/2001 | Gearhart et al. |
| 6,875,607 | B1 | 4/2005 | Reubinoff et al. |
| 7,029,913 | B2 | 4/2006 | Thomson |
| 7,220,584 | B2 | 5/2007 | Thomson et al. |
| 2002/0007051 | A1* | 1/2002 | Cheo et al. ............ 536/23.1 |

FOREIGN PATENT DOCUMENTS

| | | | |
|---|---|---|---|
| KR | WO 2005/056797 | * | 6/2005 |
| WO | WO 2009/091659 A3 | | 7/2009 |

OTHER PUBLICATIONS

Invitrogen, Inc., 2001 Product Catalog.*
Lin et al. Meth. Mol. Biol., Humana Press, Totowa NJ. 2006; (342)321-334 Ed. Ying, S.*
Lin et al. miRNA Protocols Humana Press Totowa NJ. 2006;295-312 Ed. Ying, S.*
Thomson et al., "Embryonic Stem Cell Lines Derived from Human Blastocysts," Science, vol. 282, Nov. 1998, pp. 1145-1147.
Takahashi et al., "Induction of Pluripotent Stem Cells from Mouse Embryonic and Adult Fibroblast Cultures by Defined Factors," Cell, vol. 126, Aug. 2006, pp. 663-676.
Okita et al., "Generation of germline-competent induced pluripotent stem cells," Nature, vol. 448, Jul. 2007, pp. 313-317.
Wernig et al., "In vitro reprogramming of fibroblasts into a pluripotent ES-cell-like state," Nature, vol. 448, Jul. 2007, pp. 318-324.
Yu et al., "Induced Pluripotent Stem Cell Lines Derived from Human Somatic Cells," Science, vol. 318, Dec. 2007, pp. 1917-1920.
Meissner et al., "Generation of nuclear transfer-derived pluripotent ES cells from cloned Cdx2-deficient blastocysts," Nature, vol. 439, Jan. 2006, pp. 212-215.
Hanna et al., "Treatment of Sickle Cell Anemia Mouse Model with iPS Cells Generated from Autologous Skin," Science, Dec. 2007, vol. 318, pp. 1920-1923.
Suh et al., "Human embryonic stem cells express a unique set of microRNAs," Developmental Biology, vol. 270, 2004, pp. 488-498.
Tang et al., "Maternal microRNAs are essential for mouse zygotic development," Genes & Development, vol. 21, pp. 644-648 (2007).
Murchison et al., "Critical roles for Dicer in the female germline," Genes & Development, vol. 21, pp. 682-693 (2007).

(Continued)

*Primary Examiner* — Doug Schultz
(74) *Attorney, Agent, or Firm* — Knobbe Martens Olson & Bear LLP

(57) ABSTRACT

This invention generally relates to a method for developing, generating and selecting human embryonic stem (hES)-like pluripotent cells using transgenic expression of intronic microRNA-like RNA agents. More particularly, the present invention relates to a method and composition for generating a non-naturally occurring intron and its intronic components capable of being processed into mir-302-like RNA molecules in mammalian cells and thus inducing certain specific gene silencing effects on differentiation-related and fate-determinant genes of the cells, resulting in reprogramming the cells into a pluripotent embryonic stem (ES)-cell-like state. The ES-like cells so obtained are strongly express hES cell markers, such as Oct3/4, SSEA-3 and SSEA-4, and can be guided into various tissue cell types by treating certain hormones and/or growth factors under a feeder-free cell culture condition in vitro, which may be used for transplantation and gene therapies. Therefore, the present invention offers a simple, effective and safe gene manipulation approach for not only reprogramming somatic cells into ES-like pluripotent cells but also facilitating the maintenance of pluripotent and renewal properties of ES cells under a feeder-free cell culture condition, preventing the tedious retroviral insertion of four large transcription factor genes into one single cell as used in the previous iPS methods.

32 Claims, 10 Drawing Sheets

(56) References Cited

OTHER PUBLICATIONS

Ghosh et al., "Coupled in virto synthesis and splicing of RNA polymerase II transcripts," RNA, (2000), vol. 6, pp. 1325-1334.
Lin et al., "Novel RNAi Therapy—Intron—Derived MicroRNA Drugs," Drug Design Reviews—Online, 2004, vol. 1, pp. 247-255.
Lin et al., "A novel RNA splicing-mediated gene silencing mechanism potential for genome evolution," Biochemical and Biophysical Research Communications, vol. 310, 2003, pp. 754-760.
Lin et al., "Asymmetry of intronic pre-miRNA structures in functional RISC assembly," Gene, vol. 356, 2005, pp. 32-38.
Lin et al., "Gene Silencing in Vitro and In Vivo Using Intronic MicroRNAs," Methods in Molecular Biology, vol. 342, pp. 295-312 (2006).
Lin et al., "Transgene-Like Animal Models Using Intronic MicroRNAs," Methods in Molecular Biology, vol. 342, pp. 321-334 (2006).
Lin et al., "Intron-mediated RNA interference and microRNA (miRNA)," Frontiers in Bioscience, vol. 13, Jan. 2008, pp. 2216-2230.
Tang, "siRNA and miRNA: an insight into RISCs," Trends in Biochemical Sciences, vol. 30, No. 2, Feb. 2005, pp. 106-114.
Lee et al., "The nuclear RNase III Drosha initiates microRNA processing," Nature, vol. 425, Sep. 2003, pp. 415-419.
Lewin, Genes, Seventh Edition, Oxford University press, 2000, pp. 688-690.
Scholer et al., "A family of octamer-specific proteins present during mouse embryogenesis: evidence for germline-specific expression of an Oct factor," The EMBO Journal, vol. 8, No. 9, 1989, pp. 2543-2550.
Rosner et al., "A POU-domain transcription factor in early stem cells and germ cells of the mammalian embryo," Nature, vol. 345, Jun. 1990, pp. 686-692.
Solter et al., "Monoclonal antibody defining a stage-specific mouse embryonic antigen (SSEA-1)," Proc. Natl. Acad. Sci. USA, vol. 75, No. 11, Nov. 1978, pp. 5565-5569.
Shevinsky et al., "Monoclonal Antibody to Murine Embryos Defines a Stage-Specific Embryonic Antigen Expressed on Mouse Embryos and Human Teratocarcinoma Cells," Cell, vol. 30, Oct. 1982, pp. 697-705.
Boyer et al., "Core Transcriptional Regulatory Circuitry in Human Embryonic Stem Cells," Cell, vol. 122, Sep. 2005, pp. 947-956.
Hochedlinger et al., "Nuclear reprogramming and pluripotency," Nature, vol. 44, Jun. 2006, pp. 1061-1067.
Stitzel et al., "Regulation of the Oocyte-to-Zygote Transition," Science, vol. 316, Apr. 2007, pp. 407-408.
O'Farrell et al., "Embryonic Cleavage Cycles: How Is a Mouse Like a Fly?," Current Biology, vol. 14, Jan. 2004, R35-R45.
Card et al., "Oct4/Sox2-regulated miR-302 targets cyclin D1 in human embryonic stem cells," Molecular and Cellular Biology, American Society for Microbiology, vol. 28, No. 20, XP002577530, Oct. 1, 2008, pp. 6426-6438.
Lin et al., "Mir-302 reprograms human skin cancer cells into a pluripotent ES-cell-like state," RNA, vol. 14, No. 10, XP009108022, Aug. 28, 2008, pp. 2115-2124.
Lin et al., "Role of mir-302 MicroRNA family in stem cell pluripotency and renewal," Current Perspectives in microRNAs (miRNA), XP009121067, Aug. 1, 2008, pp. 167-185.
Notification of Transmittal of the International Search Report and the Written Opinion (PCT/ISA/220, PCT/ISA/210 and PCT/ISA/237) mailed Sep. 3, 2010 in PCT/US2010/037252.
Scheel et al., "Immunofluorescence-based screening identifies germ cell associated microRNA 302 as an antagonist to p63 expression," Cell Cycle, vol. 8, No. 9, XP002597622, May 1, 2009, pp. 1426-1432.

* cited by examiner

A

Sample A = Colo    Sample B = Colo+mir-302    B/A (Cy5/Cy3)

B

Call list (differentially expressed transcripts with p-value < 0.01)

| No. | Probe_ID | Sample A Signal | Sample B Signal | log2 (Sample B / Sample A) |
|---|---|---|---|---|
| 1 | hsa-miR-302b | 67.18 | 28,423.66 | 8.78 |
| 2 | hsa-miR-302d | 55.69 | 18,679.25 | 8.38 |
| 3 | hsa-miR-302a | 49.21 | 14,840.17 | 8.20 |
| 4 | hsa-miR-302a* | 42.91 | 13,875.22 | 8.16 |
| 5 | hsa-miR-302c | 33.38 | 8,641.02 | 7.99 |
| 6 | hsa-miR-9 | 1.00 | 250.28 | 7.97 |
| 7 | hsa-miR-346 | 4,392.06 | 27.61 | -7.25 |
| 8 | hsa-miR-374 | 17.34 | 2,720.12 | 7.22 |
| 9 | hsa-miR-612 | 1,630.33 | 13.11 | -6.94 |
| 10 | hsa-miR-20b | 42.99 | 5,270.39 | 6.94 |
| 11 | hsa-miR-363 | 7.29 | 760.52 | 6.83 |
| 12 | hsa-miR-542-5p | 136.52 | 1.63 | -6.50 |
| 13 | hsa-miR-376a | 5.77 | 494.89 | 6.45 |
| 14 | hsa-miR-517a | 10.20 | 737.14 | 6.24 |
| 15 | hsa-miR-20a | 95.17 | 7,200.26 | 6.21 |
| 16 | hsa-miR-516-5p | 9.43 | 601.21 | 6.11 |
| 17 | hsa-miR-517b | 8.44 | 573.21 | 6.06 |
| 18 | hsa-miR-526a | 4.22 | 278.40 | 6.05 |
| 19 | hsa-miR-17-5p | 97.58 | 6,656.73 | 6.04 |
| 20 | hsa-miR-594 | 9.77 | 648.09 | 5.96 |

GENERATION OF HUMAN EMBRYONIC STEM-LIKE CELLS USING INTRONIC RNA

CLAIM OF THE PRIORITY

The present application claims priority to the U.S. Provisional Application Ser. No. 61/000,797 filed on Oct. 29, 2007, entitled "Novel Cosmetic Designs and Products Using Intronic RNA". The present application also claims priority to U.S. Provisional Application Ser. No. 61/007,867 filed on Dec. 17, 2007, entitled "Generation of Human Embryonic Stem-Like Cells Using Intronic RNA" and U.S. Provisional Application Ser. No. 61/006,179 filed on Dec. 28, 2007, entitled "Generation of Human Embryonic Stem-Like Cells Using Intronic RNA". Furthermore, the present application is a continuation-in-part application of the U.S. patent application Ser. No. 10/439,262 filed on May 15, 2003, entitled "RNA-Splicing and Processing-Directed Gene Silencing and the Relative Applications Thereof", and Ser. No. 11/278,143 filed on Mar. 31, 2006, entitled "Novel Transgenic Methods Using Intronic RNA", which are hereby incorporated by reference as if fully set forth herein.

FIELD OF THE INVENTION

This invention generally relates to a means and method for developing, generating and selecting human embryonic stem (hES)-like cells using transgenic expression of intronic hairpin RNA agents. More particularly, the present invention relates to a method and composition for generating a non-naturally occurring intron and its intronic components capable of being processed into small hairpin-like precursor microRNA (pre-miRNA) molecules in human cells and thus inducing certain specific gene silencing effects on differentiation-related and fate-determinant genes of the cells, resulting in reprogramming the cells into a pluripotent embryonic stem (ES)-cell-like state. Preferably, the hairpin-like pre-miRNA molecules include mir-302a, mir-302b, mir-302c, mir-302d, and their manually re-designed precursor homologues as well as a combination thereof.

BACKGROUND OF THE INVENTION

Recent research in human stem cells has shown a highly promising potential in transplantation therapy. Nevertheless, the sources for cloning human stem cells are limited and very difficult to control their purity and quality. In 1998, James Thomson et al. (e.g. U.S. Pat. No. 5,843,780, U.S. Pat. No. 6,200,806, U.S. Pat. No. 7,029,913, and No. 7,220,584) have isolated the first human embryonic stem (hES) cell line from the blastocysts of human embryos (Thomson et al., (1998) *Science* 282: 1145-1147). H1 and H9 are two typical cell lines derived from these isolated hES cells. Two years later, Gearhart et al. (e.g. U.S. Pat. No. 6,090,622, U.S. Pat. No. 6,245,566, and U.S. Pat. No. 6,331,406) also develop a means and method to isolate hES-like primordial germ cells from post-blastocyst human embryos. Because the way of these embryonic stem cell isolation methods must destroy the original embryos, many ethical and humanity concerns have been raised to debate the righteousness of using the hES cell lines so obtained for clinical therapy.

In recent years, more and more concerns about the safety issue of using the isolated hES cell lines have been noticed. For example, since the culture conditions for maintaining the long-lasting pluripotent stem cell state of these hES cell lines require some unidentified factors released from surrounding "feeder" fibroblast cells, the hES cells are usually cultured on a mouse or human fibroblast feeder layer. Prior arts attempting this approach include U.S. Pat. No. 6,875,607 to Reubinoff et al. However, the fibroblast feeder cells carry totally different antigen characteristics, which may very likely contaminate the hES cells and cause immune rejection in patients. Meantime, although some feeder-free culture conditions have also been developed, none of these feeder-free methods are capable of maintaining a stable, undifferentiated stem cell state of the hES cells for a long time. This problem is actually related to another drawback of the isolated hES cells, which is their impurity. None of the currently available hES cell lines can reach a 100% pure population in culture conditions. Even under the best feeder culture condition, an uncertain rate (about 3-5% or more) of the hES cells tend to differentiate into other cell types and lose their stem cell properties. One of the most frequently observed cell types differentiated from the hES cells is teratoma. Teratoma is a tumor derived from human germ line cells, often containing multiple cancerous-look cell types similar to embryonic endoderm, mesoderm and ectoderm tissues. Therefore, how to prevent the feeder contamination and increase stem cell purity are two main tasks for the present stem cell research.

Induced pluripotent stem (iPS) cells are newly introduced by Takahashi and Yamanaka in 2006 (*Cell* 126: 663-676). Using transgenically delivery of four transcription factor genes (Oct3/4, Sox2, c-Myc, Klf4) into mouse fibroblasts, they successfully reprogram and transform the somatic fibroblast cells into embryonic stem (ES)-like pluripotent cells in vitro. In 2007, the behavioral properties of these iPS cells are confirmed to be similar to those of the mouse embryonic stem (mES) cells (Okita et al., (2007) *Nature* 448: 313-317; Wernig et al., (2007) *Nature* 448: 318-324). Meantime, Yu et al. develop more new iPS cell lines from human fibroblast cells, using a similar approach with four other transgenes such as Oct4, Sox2, Nanog, and LIN28 (Yu et al., (2007) *Science* 318: 1917-1920). The utilization of iPS cells not only solves the ethical and impurity problems of the previous hES cells but also provides a potential patient-friendly therapy if in conjunction with the somatic cell nuclear transfer (SCNT) technology (Meissner et al., (2006) *Nature* 439: 212-215). Such an iPS cell-based SCNT therapy has been proven to be successful in treating sickle cell anemia in a transgenic mouse model (Hanna et al., (2007) *Science* 318: 1920-1923). Yet, the advance of iPS cell applications is not perfect. Two problems emerge during the processes of iPS cell generation; one is the use of retroviral transgenes and the other is the use of oncogenes (e.g. c-Myc). Retroviral transfection is the only effective means to simultaneously and transgenically deliver the four full-length genes into a targeted somatic cell, whereas the random insertion of retroviral vectors into the transfected cell genome may also affect other non-targeted genes and cause unexpected results. This is particularly dangerous when one or more of the delivered genes is an oncogene.

Simultaneous delivery of four full-length transgenes into one single cell is very difficult to control precisely. However, the iPS cell technology actually requires the use of multiple transcription factors to offset or coordinate the signal transduction among each other and certain other developmental factors. Although detail mechanism is still unclear, the combined gene effects of Oct4-Sox2-c-Myc-Klf4 or Oct4-Sox2-Nanog-LIN28 seemingly result in a cancellation of developmental signals required for early cell differentiation. Despite the embryonic stem marker Oct4, all other genes used in iPS cell generation are involved in certain developmental lineages. They are usually presented in different embryonic stages and/or locations to guide the specific cell differentiation. By misplacing them together, the disturbance of these developmental signals somehow stops the cell differentiation and then retreats the host cell back to an ES-like state until another new developmental signal is given again. This method works but is not natural. In natural fertilized eggs, maternal materials are responsible for the regulation of stem cell maintenance and replication. That is why embryonic cells before the 128-cell stage are all the same and all totipotent. Maternal materials are generated during oogenesis and deposited in a mature oocyte required for early embryonic development. In a mouse oocyte, RNAs occupy a large volume of maternal materials, corresponding to about 45% of the whole genomic transcriptome (Stitzel et al., (2007) *Science* 316: 407-408). During maternal-zygotic transition, these maternal RNAs are quickly degraded and the transcription of zygotic genes starts as early as at the two-cell stage to produce signals for further embryonic development (O'Farrell et al., (2004) *Curr. Biol.* 14: R35-45). It is conceivable that many of the maternal RNAs are inhibitors of the zygotic gene products in order to prevent developmental signals and maintain the totipotent/pluripotent cell division at the most early embryonic stage. Therefore, the secret of stem cell maintenance and renewal should reside in maternal materials rather than the developmental signals, which are shown much later than the pluripotent embryonic stem cell stage.

In sum, in order to generate and maintain human embryonic stem (hES)-like cells mimicking the natural way of maternal materials, a new strategy is highly desired for transgenically delivering the isolated maternal material(s) into a human stem or somatic cell, so as to maintain the stem cell property or to reprogram the somatic cell into a hES-like cell state. Therefore, there remains a need for an effective, simple and safe transgenic method as well as agent composition for generating hES-like cells, using maternal materials, particularly the maternal RNAs.

SUMMARY OF THE INVENTION

The present invention is a transgenic method for developing, generating and selecting embryonic stem (ES)-like cells using intronic expression of hairpin-like microRNA (miRNA) agents, such as mir-302a, mir-302b, mir-302c, mir-302d, and their manually re-designed precursor microRNA (pre-miRNA) homologues as well as a combination thereof. MicroRNA is usually about 18-27 nucleotides (nt) in length and capable of either directly degrading its messenger RNA (mRNA) target or suppressing the translation of target proteins, depending on the complementarity between the miRNA and its target. The mir-302 family is highly conserved in all mammals, consisting of four highly homologous microRNA members (>90% homology): mir-302a, mir-302b, mir-302c, and mir-302d. The mir-302 family (mir-302s) is expressed together as a cluster in a long RNA transcript encoding mir-302b-mir-302c-mir-302a-mir-302d-mir-367 in a 5' to 3' sequential order (Suh et al., (2004) *Dev. Biol.* 270: 488-498). Although mir-367 is co-expressed within the mir-302 cluster, the actual level of mir-367 is lower than those of mir-302s. The expression of the mir-302 familial members is also found to be exclusively and extremely high in mouse oocytes and human embryonic stem cells (Tang et al., (2007) *Genes Dev.* 21: 644-648; Suh et al., (2004) *Dev. Biol.* 270: 488-498). Mouse oocytes lacking Dicer, a conserved ribonuclease required for microRNA biogenesis, arrest in the division phase of meiosis I, indicating that microRNAs play critical role in oogenesis (Murchison et al., (2007) *Genes Dev.* 21: 682-693). Thus, the mir-302 family is very likely one of the key maternal materials essential for stem cell maintenance and renewal.

Unlike the previous iPS cell technology using elevated expression of four cellular transcription factor genes, each member of the mir-302 family is able to regulate over 445 cellular genes and the mir-302 members all share almost the same target genes based on the database of the miRBase:: Sequences program (http://microrna.sanger.ac.uk/). Many of the mir-302 targeted genes are actually developmental signals involved in initiation or facilitation of early cell differentiation during embryonic development stages. Thus, the function of mir-302 is more likely to shut down or attenuate the global production of developmental signals rather than to create a disturbance among specific signaling pathways. For example, insulin-like growth factors (IGF) are potent developmental signals for the neuron-specific stem and progenitor cell lineage via either the Ras/Raf/mitogen-activated protein kinase (MAPK) or the phosphatidylinositol 3-kinase (PI3K)/ Akt signal transduction pathway. We found that over eighteen members of the IGF receptor (IGFR)-Ras/PI3K signaling pathways are strong targets for mir-302s, indicating that there is an extremely tight blockade of neuron-specific cell differentiation in mammalian oocytes and ES cells. The mir-302s bind complementarily to the homologous sequences of these targeted gene transcripts and then suppress their protein translation through the mechanism of RNA interference. Similar inhibitory effects of mir-302s on many other developmental genes involved in different tissue cell lineages are also observed. In view of these evidences, it is very likely that the mir-302 family plays a critical role in ES cell maintenance and renewal. By inhibiting the target genes essential for cell development and differentiation, mir-302s may be used to not only reprogram and transform somatic cells into ES-like cells but also maintain the pluripotent and renewal properties of embryonic stem cells.

To test the mir-302 function in stem cell generation and maintenance, the inventors use a Pol-II-based intronic miRNA expression system to transgenically express the mir-302 familial members in several kinds of human somatic cells, mimicking the native intronic miRNA biogenesis pathway (FIG. 1). Intronic miRNA biogenesis relies on a coupled interaction between nascent Pol-II-mediated pre-mRNA transcription and intron splicing/excision, occurring within certain nuclear regions proximal to genomic perichromatin fibrils (Lin et al. (2004) *Drug Design Reviews* 1: 247-255; Ghosh et al. (2000) *RNA* 6: 1325-1334). In eukaryotes, protein-coding gene transcripts, e.g. mRNAs, are produced by type-II RNA polymerases (Pol-II). The transcription of a genomic gene generates precursor messenger RNA (pre-mRNA), which contains four major parts including a 5'-untranslated region (UTR), protein-coding exons, non-coding introns and a 3'-UTR. Broadly speaking, both 5'- and 3'-UTR can be seen as a special intron. Introns occupy the largest proportion of non-coding sequences in the pre-mRNA. Each intron may be ranged up to thirty or so kilo-bases and is required to be excised out of the pre-mRNA before mRNA maturation. This process of pre-mRNA excision and intron removal is called RNA splicing, which is executed by intracellular spliceosomes. After RNA splicing, some of the intron-derived RNA fragments are further processed to form miRNA-like derivative molecules, which can effectively silence their target genes, respectively, through an RNA interference (RNAi)-like mechanism, while exons of the pre-mRNA are ligated together to form a mature mRNA for protein synthesis.

We have demonstrated that effective miRNAs can be generated from the introns of vertebrate genes, of which the biogenetic process is different from those of siRNA and intergenic miRNA (Lin et al. (2003) *Biochem Biophys Res Commun.* 310: 754-760; Lin et al. (2005) *Gene* 356: 32-38). To demonstrate such differences, FIG. 2 shows the comparison of native biogenesis and RNAi mechanisms among siRNA, intergenic (exonic) miRNA and intronic miRNA. Presumably, siRNA is formed by two perfectly complementary RNAs transcribed by two reversely position promoters from the same DNA template, then hybridized and further processing into 20-25 bp duplexes by RNaseIII endoribonucleases, namely Dicer. Different from this siRNA model, the biogenesis of intergenic miRNAs, e.g. lin-4 and let-7, involves a long non-coding precursor RNA transcript (pri-miRNA), which is directly transcribed from either Pol-II or Pol-III RNA promoters, whereas intronic pri-miRNA is co-transcribed with its encoding gene by only Pol-II and released after RNA splicing as a spliced intron. In the cell nucleus, the pri-miRNA is further excised by either Drosha-like RNases (for intergenic miRNA) or spliceosomal and exosomal components (for intronic miRNA) to form a hairpin-like stem-loop precursor, termed pre-miRNA, and then exported to cytoplasm for processing into mature miRNA by miRNA-associated Dicer. Subsequently, all three small regulatory RNAs are finally incorporated into a RNA-induced silencing complex (RISC), which contains either double strand of siRNA or the single strand of miRNA. Dicers and RISCs for siRNA and miRNA pathways are known to be different (Tang, G. (2005) *Trends Biochem Sci.* 30: 106-114). As a result, the effect of miRNA is generally more specific and less adverse than that of siRNA because only one strand is involved. On the other hand, siRNAs primarily trigger mRNA degradation, whereas miRNAs can induce either mRNA degradation or suppression of protein synthesis, or both, depending on the sequence complementarity to their targeted gene transcripts. Because the intronic miRNA pathway is well coordinated by multiple intracellular regulation systems, including Pol-II transcription, RNA splicing, exosome digestion and NMD processing, the gene silencing effect of intronic miRNA is considered to be most effective, specific and safe in all three RNAi pathways (Lin et al. (2008) *Frontiers in Bioscience* 13: 2216-2230).

Our present invention discloses a novel function of intron in the aspect of gene regulation and its relative utilities thereof. As shown in FIG. 3A and FIG. 3B, based on the intronic RNA splicing and processing mechanisms, one preferred embodiment of the present invention is a Pol-II-mediated recombinant gene expression system containing at least a splicing-competent intron, namely SpRNAi, which is able to inhibit the function of a target gene or genes with high complementarity to a certain SpRNAi sequence. The SpRNAi is co-transcribed with the precursor mRNA (pre-mRNA) of the recombinant gene by Pol-II RNA polymerases and cleaved out of SpRNAi by RNA splicing. Subsequently, the spliced SpRNAi is further processed into mature gene silencing agents, such as small hairpin RNA (shRNA) and miRNA, capable of triggering RNAi-related gene silencing. After intron removal, the exons of the recombinant gene transcript are linked together to form a mature mRNA molecule for translational synthesis of a marker or functional protein.

As shown in FIG. 3A, the essential components of the SpRNAi intron include several consensus nucleotide elements, consisting of a 5'-splice site, a branch-point motif (BrP), a poly-pyrimidine tract (PPT), and a 3'-splice site. In addition, a shRNA-like pre-miRNA sequence is inserted inside SpRNAi between the 5'-splice site and the branch-point motif (BrP). This portion of the intron would form a lariat structure during RNA splicing and processing. Further, the 3'-end of SpRNAi construct contains a multiple translational stop codon region (T codon) in order to increase the accuracy of intronic RNA splicing and NMD processing. When presented in a cytoplasmic mRNA, this T codon would signal the activation of the nonsense-mediated decay (NMD) pathway to degrade any unstructured RNA accumulation in the cell. However, the highly secondary structured shRNA and pre-miRNA insert will be preserved for further Dicer cleavage, so as to form mature siRNA and miRNA, respectively. Moreover, for intracellular expression, we manually incorporate SpRNAi construct in the DraII restriction site of a red fluorescent protein (RGFP) gene isolated from mutated chromoproteins of the coral reef *Heteractis crispa*, so as to form a recombinant SpRNAi-RGFP construct. The cleavage of RGFP at its 208th nucleotide site by the restriction enzyme DraII generates an AG-GN nucleotide break with three recessing nucleotides in each end, which will form 5'- and 3'-splice sites respectively after SpRNAi insertion. Because this intronic insertion disrupts the structure of a functional RGFP protein, which can be recovered by intron splicing, we can determine the release of intronic shRNA/miRNA and RGFP-mRNA maturation through the appearance of red RGFP around the affected cells. The RGFP gene also provides multiple exonic splicing enhancers (ESEs) to increase RNA splicing accuracy and efficiency.

In another preferred embodiment (FIG. 3B), the present invention provides a genetic engineering method for using synthetic RNA splicing and processing elements, such as 5'-splice site, branch-point motif (BrP), poly-pyrimidine tract (PPT), and 3'-splice site, to form an artificial SpRNAi containing at least a desired RNA insert for antisense RNA, shRNA and/or miRNA production. A DNA synthesizer can chemically produce and linked these elements. Alternatively, the linkage of these elements can be achieved by enzymatic restriction and ligation. The intron so obtained can be used directly for transfection into cells of interest or further incorporated into a cellular gene for co-expression along with the gene transcript (i.e. pre-mRNA) by Pol-II. During RNA splicing and mRNA maturation, the desired RNA insert will be excised and released by intracellular spliceosome, exosome and NMD mechanisms and then triggers a desired gene silencing effect on specific gene transcripts with high complementarity to the inserted RNA sequence, while the exons of the recombinant gene transcript are linked together to form mature mRNA for expression of a desirable gene function, such as translation of a reporter or marker protein selected from the group of red/green fluorescent protein (RGFP/EGFP), luciferase, lac-Z, and their derivative homologues. The presence of the reporter/marker protein is useful for locating the production of the inserted shRNA/miRNA molecules in affected cells, facilitating the identification of the desired gene silencing/RNAi effects.

In accordance with the present invention, mature mRNA formed by the linkage of exons may also be useful in conventional gene therapy to replace impaired or missing gene function, or to increase specific gene expression. In another aspect, the present invention provide novel compositions and means for inducing cellular production of gene silencing molecules through intronic RNA splicing and processing mechanisms to elicit either antisense-mediated gene knockout or RNA interference (RNAi) effects, which are useful for inhibiting targeted gene function. The intron-derived gene silencing molecules so obtained include antisense RNA, ribozyme, short temporary RNA (stRNA), double-stranded RNA (dsRNA), small interfering RNA (siRNA), tiny non-coding RNA (tncRNA), short hairpin RNA (shRNA), microRNA (miRNA), and RNAi-associated precursor RNA constructs (pri-/pre-miRNA). The use of these intronic RNA-derived gene silencing agents is a powerful tool for targeting and silencing unwanted genes selected from the group consisting of pathogenic transgenes, viral genes, mutant genes, oncogenes, disease-related small RNA genes and any other types of protein-coding as well as non-coding genes.

Using this Pol-II-mediated SpRNAi-RGFP expression system of the present invention, we have successfully generated mature shRNA and miRNA with full gene silencing capacity in human prostate cancer LNCaP, human cervical cancer HeLa and rat neuronal stem HCN-A94-2 cells (Lin et al. (2006a) *Methods Mol. Biol.* 342: 295-312) as well as in zebrafish, chicken and mouse in vivo (Lin et al. (2006b) *Methods Mol. Biol.* 342: 321-334). We have tested different pre-miRNA insert constructs targeting against green EGFP and other cellular gene transcript and expression in zebrafish and various human cell lines, and have learned that effective gene silencing miRNAs are derived from the 5'-proximity of the intron sequence between the 5'-splice site and the branching point. As shown in FIG. 3C, a strong gene silencing effect occurs only in the transfection of anti-EGFP pre-miRNA insert (lane 4), whereas no such effect can be detected in those of other inserts indicated by lanes from left to right: 1, blank vector control (Ctl); 2, pre-miRNA insert targeting HIV-p24 (mock); 3, antisense EGFP insert without the hairpin loop structure (anti); and 5, reverse anti-EGFP pre-miRNA sequence which is completely complementary to the anti-EGFP pre-miRNA (miR*). No effect was detected on off-target genes, such as marker RGFP and house-keeping β-actin, suggesting that such intronic miRNA-mediated RNA interference (RNAi) is highly target-specific. To further confirm the role of RNA splicing in this intronic RNAi effect, we have also tested three different SpRNAi-RGFP expression systems as shown in FIG. 3D by lanes from left to right: 1, vector expressing intron-free RGFP (SpRNAi-RGFP expression system without any pre-miRNA insert); 2, SpRNAi-RGFP expression system expressing RGFP with an intronic anti-EGFP pre-miRNA insert; and 3, SpRNAi-RGFP expression system similar to the 2 construct but with a defective 5'-splice site in SpRNAi. As a result, Northern blot analysis shows that mature miRNA is released only from the spliced intron of the SpRNAi-RGFP expression system 2 construct (lane 2), which is exactly identical to SpRNAi construct with the anti-EGFP pre-miRNA insert (lane 4) in the FIG. 3C, indicating the requirement of cellular RNA splicing for intronic miRNA biogenesis.

After the above understanding, we have further determined the optimal structural design of the pre-miRNA inserts for inducing maximal gene silencing effects and learned that a strong structural bias exists in the cellular selection of a mature miRNA strand during assembly of the RNAi effector, the RNA-induced gene silencing complex (RISC) (Lin et al. (2005) *Gene* 356: 32-38). RISC is a protein-RNA complex that directs either target gene transcript degradation or translational repression through the RNAi mechanism. Formation of siRNA duplexes plays a key role in assembly of the siRNA-associated RISC. The two strands of the siRNA duplex are functionally asymmetric, but assembly into the RISC complex is preferential for only one strand. Such preference is determined by the thermodynamic stability of each 5'-end base-pairing in the strand. Based on this siRNA model, the formation of miRNA and its complementary miRNA (miRNA*) duplexes was thought to be an essential step in the assembly of miRNA-associated RISC. If this were true, no functional bias would be observed in the stem-loop structure of a pre-miRNA. Nevertheless, we observed that the stem-loop orientation of the intronic pre-miRNA is involved in the strand selection of a mature miRNA for RISC assembly in zebrafish.

As shown in FIG. 4A, we have constructed two different intronic miRNA-inserted SpRNAi-RGFP expression vectors containing a pair of symmetric pre-miRNA constructs, namely miRNA*-stemloop-miRNA [1] and miRNA-stemloop-miRNA* [2], respectively. Both pre-miRNAs contain the same double-stranded stem-arm structure, which is directed against the EGFP nucleotide 280-302 sequence. In definition here, miRNA refers the exactly complete sequence of a mature miRNA, while miRNA* refers the reverse nucleotide sequence complementary to the mature miRNA sequence. After liposomal transfection of these miRNA-expressing SpRNAi-RGFP vectors (60 μg each) into two-week-old zebrafish larvae for 24 hours (Lin et al. (2005) *Gene* 356: 32-38), we have isolated the zebrafish small RNAs using mirVana miRNA isolation columns (Ambion, Austin, Tex.) and then precipitated all the potential miRNAs matched to the targeted EGFP region by latex beads containing the target sequence. After sequencing, one effective miRNA identity, miR-EGFP(280-302), is identified to be active in the transfection of the 5'-miRNA-stemloop-miRNA*-3' [2] construct, as shown in FIG. 4B (gray-shading sequences). Since the mature miRNA is detected only in the zebrafish transfected by the 5'-miRNA-stemloop-miRNA*-3' [2] construct, the miRNA-associated RISC may preferably interact with the construct [2] rather than the [1] pre-miRNA, demonstrating the existence of a structural bias for intronic miRNA-RISC assembly. In this experiment, we use an actin-promoter-driven Tg(UAS:gfp) strain zebrafish, namely Tg(actin-GAL4:UAS-gfp), which constitutively express a green fluorescent EGFP protein in almost all cell types of the fish body. As shown in FIG. 4C, transfection of the SpRNAi-RGFP vector in these zebrafish silences the target EGFP and co-expresses a red fluorescent marker protein RGFP, serving as a positive indicator for intronic miRNA generation in the affected cells. The gene silencing effect in the gastrointestinal (GI) tract is somehow lower than other tissues, probably due to the high RNase activity in this region. Based on further Western blot analysis (FIG. 4D), the indicator RGFP protein expression is detected in both of the fish transfected with either 5'-miRNA*-stemloop-miRNA-3' [1] or 5'-miRNA-stemloop-miRNA*-3' [2] pre-miRNA, whereas gene silencing of the target EGFP expression only occurs in the fish transfected with the 5'-miRNA-stemloop-miRNA*-3' pre-miRNA [2] construct, confirming the result of FIG. 4C. Because thermostability of the 5'-end stem-arm of both pre-miRNA constructs is the same, we conclude that the stem-loop of the intronic pre-miRNA is involved in the strand selection of a mature miRNA sequence during RISC assembly. Given that the cleavage site of Dicer in the stem-arm is known to determine the strand selection of mature miRNA (Lee et al. (2003) *Nature* 425: 415-419), the stem-loop of an intronic pre-miRNA may function as a determinant for the recognition of the special cleavage site.

In the above early design, because the over sizes of many native pre-miRNA stem-loop structures cannot fit in the SpRNAi-RGFP expression vector for efficient expression, we must use a short tRNA$^{met}$ loop (i.e. 5'-(A/U)UC- CAAGGGGG-3') (SEQ ID NO: 29) to replace the native pre-miRNA loops. The tRNA$^{met}$ loop has been shown to efficiently facilitate the export of designed miRNAs from nucleus to cytoplasm through the same Ran-GTP and Exportin-5 transporting mechanisms (Lin et al. (2005) *Gene* 356: 32-38). Currently, the present invention uses a pair of manually improved pre-mir-302 loops (i.e. 5'-GCTAAGC-CAGGC-3' (SEQ. ID. NO. 1) and 5'-GCCTGGCTTAGC-3' (SEQ. ID. NO. 2)), which provide the same nuclear export efficiency as the native pre-miRNAs but not interfere with the tRNA exportation. The design of these new pre-miRNA loops is based on a mimicking modification of short stem-loops of mir-302s, which are highly expressed in embryonic stem cells but not in other differentiated tissue cells. Thus, the use of these man-made pre-miRNA loops will not interfere with the native miRNA pathway in our body.

For pre-miRNA insertion, because the intronic insertion site of the recombinant SpRNAi-RGFP construct is flanked with a PvuI and an MluI restriction site at its 5'- and 3'-ends, respectively, the primary intronic insert can be easily removed and replaced by various gene-specific pre-miRNA inserts (e.g. anti-EGFP and mir-302 pre-miRNA) possessing matched cohesive ends. By changing the pre-miRNA inserts directed against different gene transcripts, this intronic miRNA generation system can be served as a powerful tool for inducing target gene silencing in vitro and in vivo. For confirming the correct insert size, the pre-miRNA-inserted SpRNAi-RGFP construct (10 ng) can be amplified by a polymerase chain reaction (PCR) with a pair of oligonucleotide primers (i.e. 5'-CTCGAGCATG GTGAGCGGCC TGCTGAA-3' and 5'-TCTAGAAGTT GGCCTTCTCG GGCAGGT-3' SEQ ID NOS: 23 and 24, respectively) for 25 cycles at 94° C., 52° C. and then 70° C. each for 1 min. The resulting PCR products are fractionated on a 2% agarose gel, and then extracted and purified by gel extraction kit (Qiagen, CA) for sequencing confirmation.

The present invention adopts the proof-of-principle design of the Pol-II-mediated SpRNAi-RGFP expression system and uses it for transgenically expressing one or more mir-302 familial members (mir-302s) in human and/or mouse cells. In one preferred embodiment, the present invention provides a method for using a non-naturally occurring intron and its components capable of being processed into mir-302-like RNA molecules by human and/or mouse cells and thus inducing specific gene silencing effects on developmental and differentiation-related genes in the cells, comprising the steps of: a) providing: i) a cell substrate expressing a plurality of developmental and differentiation-related genes targeted by mir-302s, and ii) an expression-competent composition comprising a recombinant gene capable of producing an intron-driven primary RNA transcript, which is in turn able to generate a manually designed mir-302-like RNA molecule from the intron through intracellular RNA splicing and/or processing mechanisms and thus to knock down the target gene expressions or to suppress the target gene functions in the cell substrate; b) treating the cell substrate with the composition under conditions such that the target gene functions in the cell substrate are inhibited. After that, the cell substrate is transformed into an embryonic stem (ES)-like cell, which expresses embryonic stem cell markers such as Oct3/4, SSEA3 and SSEA4. The cell substrate expresses the target genes either in vitro, ex vivo or in vivo. In broad definition, the intron is a non-coding sequence of a gene, including in-frame intron, 5'-untranslated region (5'-UTR) and 3'-UTR. In one aspect, the manually designed mir-302-like RNA molecule contains the first seventeen nucleotides (e.g. 5'-UAAGUGCUUC CAUGUUU-3' (SEQ. ID. NO. 3)) of the mir-302a, mir-302b, mir-302c or mir-302d sequence. All of these mir-302 familial miRNAs possess identical first 17 nucleotides in their 5'-end sequences. Alternatively, the manually designed mir-302-like RNA molecule can also be incorporated into the intron region of a cellular gene for co-expression with such gene. In general, this kind of intronic insertion technology includes plasmid-like transgene transfection, homologous recombination, transgene incorporation, transposon delivery, jumping gene integration and retroviral infection a combination thereof.

In another aspect, the recombinant gene of the present invention expresses a construct reminiscent of a pre-mRNA structure. The recombinant gene is consisted of two major different parts: exon and intron. The exon part is ligated after RNA splicing to form a functional mRNA and protein for identification of the intronic RNA release, while the intron is spliced out of the recombinant gene transcript and further processed into a desired intronic RNA molecule, serving as a gene silencing effector, including antisense RNA, miRNA, shRNA, siRNA, dsRNA and their precursors (i.e. pre-miRNA and piRNA). These desired intronic RNA molecules may comprise a hairpin-like stem-loop structure containing a sequence motif homologous to 5'-GCTAAGCCAG GC-3' (SEQ. ID. NO. 1) or 5'-GCCTGGCTTA GC-3' (SEQ. ID. NO. 2), which facilitates not only accurate excision of the desired RNA molecule out of the intron but also nuclear exportation of the desired RNA molecule to the cell cytoplasm. Also, the stem-arms of these intron-derived RNA molecules contain homology or complementarity, or both, to a target gene or a coding sequence of the target gene transcript. The homologous or complementary sequences of the desired RNA molecules are sized from about 15 to about 1,500 nucleotide bases, most preferably in between about 18 to about 27 nucleotide bases. The homology and/or complementarity rate of the desired intronic RNA molecule to the target gene sequence is ranged from about 30~100%, more preferably 35~49%, for a desired hairpin-like intronic RNA and 90~100% for a linear intronic RNA.

In addition, the 5'-end of the non-naturally occurring intron contains a 5'-splice site homologous to either 5'-GTAAGAGK-3' (SEQ. ID. NO. 4) or GU(A/G)AGU motifs (i.e. 5'-GTAAGAGGAT-3' (SEQ ID NO: 30), 5'-GTAAGAGT-3', 5'-GTAGAGT-3' and 5'-GTAAGT-3'), while its 3'-end is a 3'-splice site that is homologous to either GWKSCYRCAG (SEQ. ID. NO. 5) or CT(A/G)A(C/T)NG motifs (i.e. 5'-GATATCCTGC AG-3'(SEQ ID NO: 31), 5'-GGCTGCAG-3' and 5'-CCACAG-3'). Moreover, a branch point sequence is located between the 5'- and 3'-splice sites, containing homology to 5'-TACTWAY-3' (SEQ. ID. NO. 6) motifs, such as 5'-TACTAAC-3' and 5'-TACTTAT-3'. The adenosine "A" nucleotide of the branch-point sequence forms a part of (2'-5')-linked lariat intron RNA by cellular (2'-5')-oligoadenylate synthetases and spliceosomes in almost all spliceosomal introns. Furthermore, a poly-pyrimidine tract is closely located between the branch-point and 3'-splice site, containing a high T or C content oligonucleotide sequence homologous to either 5'-(TY)m(C/-)(T)nS(C/-)-3' (SEQ. ID. NO. 7) or 5'-(TC) nNCTAG(G/-)-3' (SEQ. ID. NO. 8) motifs. The symbols of "m" and "n" indicate multiple repeats ≥1; most preferably, the m number is equal to 1~3 and the n number is equal to 7~12. The symbol "-" refers an empty nucleotide in the sequence. There are also some linker nucleotide sequences for the connection of all these intron components. Based on the guideline of 37 CFR 1.822 for symbols and format to be used for nucleotide and/or amino acid sequence data, the symbol W refers to an adenine (A) or thymine (T)/uracil (U), the symbol K refers to a guanine (G) or thymine (T)/uracil (U), the symbol S refers to a cytosine (C) or guanine (G), the symbol Y refers to a cytosine (C) or thymine (T)/uracil (U), the symbol R refers to an adenine (A) or guanine (G), and the symbol N refers to an adenine (A), cytosine (C), guanine (G) or thymine (T)/uracil (U)."

In another preferred embodiment of the present invention, the recombinant gene composition can be incorporated into an expression-competent vector for gene transfection. The expression-competent vector is selected from a group consisting of DNA transgenes, plasmids, jumping genes, transposons, retrotransposons, retroviral vectors, lentiviral vectors, adenoviral (AMV) vectors, adeno-associated viral (AAV) vectors, modified hepatitis-viral (HBV) vectors, and cytomegalovirus (CMV)-associated viral vectors. During transfection of the SpRNAi-RGFP construct, multiple vectors expressing different intronic gene silencing effectors may be used to achieve gene silencing effects on multiple target genes. Alternatively, multiple gene silencing effectors may be generated from the intronic hairpin RNA insert of SpRNAi-RGFP construct to provide multiple gene silencing effects. The advantage of this strategy is in its delivery stability through the use of vector-based transgene transfection and viral infection, providing a stable and relatively long-term effect of specific gene silencing. In one aspect, the present invention via cellular RNA splicing and processing mechanisms can produce RNAi-related gene silencing effectors, including siRNA, miRNA and/or shRNA, under the control of a RNA promoter selected from the group consisting of type-II RNA polymerase (Pol-II), type-III RNA polymerase (Pol-III) and viral promoters. The viral promoters are Pol-II-like RNA promoters isolated from cytomegalovirus (CMV), retrovirus long-terminal region (LTR), hepatitis B virus (HBV), adenovirus (AMV), and adeno-associated virus (AAV). For example, a lentiviral LTR promoter is sufficient to provide up to $5 \times 10^5$ copies of pre-mature mRNA per cell. It is also feasible to insert a drug-sensitive repressor in front of the lentiviral promoter in order to control gene silencing effectors' transcription rate. The repressor can be inhibited by a chemical drug or antibiotics selected from the group of G418, tetracycline, neomycin, ampicillin, kanamycin, and their derivatives, etc.

The present invention provides a novel means and method of producing intronic RNA in cell as well as in vivo through RNA splicing and processing mechanisms, preferably leading to the generation of mature siRNA, miRNA and shRNA capable of inducing RNAi-associated gene silencing effects. The desired siRNA, miRNA and/or shRNA can be produced in single unit or in multiple units, depending on how the cellular mechanisms express and process the intronic precursor miRNA/shRNA inserts of the present invention. For example, it has been reported that the ectopic expression of one anti-EGFP pre-miRNA inserted intron in zebrafish, as shown in FIG. 3A, actually generates two differently sized mature miRNAs, such as miR-EGFP(282/300) and miR-EGFP(280-302), indicating that one gene-silencing RNA insert of SpRNAi can generate more than one gene-silencing effectors. Same or different gene-silencing effectors can be generated in either sense or antisense conformation, or both, complementary to the target gene transcript(s). In certain cases, intronic gene-silencing effectors can hybridize with a target gene transcript (i.e. mRNA) to form a double-stranded RNA (dsRNA) for triggering secondary RNAi effects. Because intronic gene-silencing effectors are constantly produced by the expression-competent vectors of the present invention, it will alleviate the concerns of fast small RNA degradation for in vivo applications.

In addition to the general function of the present invention for stem cell generation, the potential applications of the present invention includes maintenance of feeder-free human embryonic stem cell lines and keep such cells lines from differentiation, in vitro cloning and culture of adult stem cell lines, purification of homologous stem cell populations, and transplantation therapy using the stem cells so obtained. The present invention can also be used as a tool for studying stem cell function and mechanism or providing a composition and method for altering the characteristics of a stem cell toward specific utilization. In other embodiments, the embryonic stem (ES)-like pluripotent cells of the present invention can be generated from the group of normal and cancerous somatic cells as well as adult stem cells of mammals, such as human, monkey, rat and mice.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The FIG. 1 depicts the biogenesis of native intronic microRNA (miRNA) that is co-transcribed with precursor messenger RNA (pre-mRNA) by Pol-II and cleaved out of the pre-mRNA by RNA splicing, while the ligated exons become a mature messenger RNA (mRNA) for protein synthesis. The spliced intronic miRNA with an antisense or a hairpin-like secondary structure is further processed into mature miRNA capable of triggering RNAi-related gene silencing effects. Thus, we designed an artificial intron containing at least a precursor microRNA (pre-miRNA) structure, namely SpRNAi, mimicking the biogenesis of the native intronic miRNA (FIGS. 3A and 3B). The SpRNAi is incorporated into a cellular or recombinant gene, which is expressed by type-II RNA polymerases (Pol-II) under the control of either Pol-II or viral RNA promoter (P). Upon intracellular transcription, the gene transcript so produced is subjected to RNA splicing and processing events and therefore releases the pre-designed, intronic RNA molecule in the transfected cell. In certain cases, the desired RNA molecule is an antisense RNA construct that can be served as antisense oligonucleotide probes for gene knockdown. In another cases, the desired RNA molecule consists of small antisense and sense RNA fragments to function as double-stranded siRNA for RNAi induction. In some other cases, the desired RNA molecule is a hairpin-like RNA construct capable of causing RNAi-associated gene silencing effects.

Figure 1:
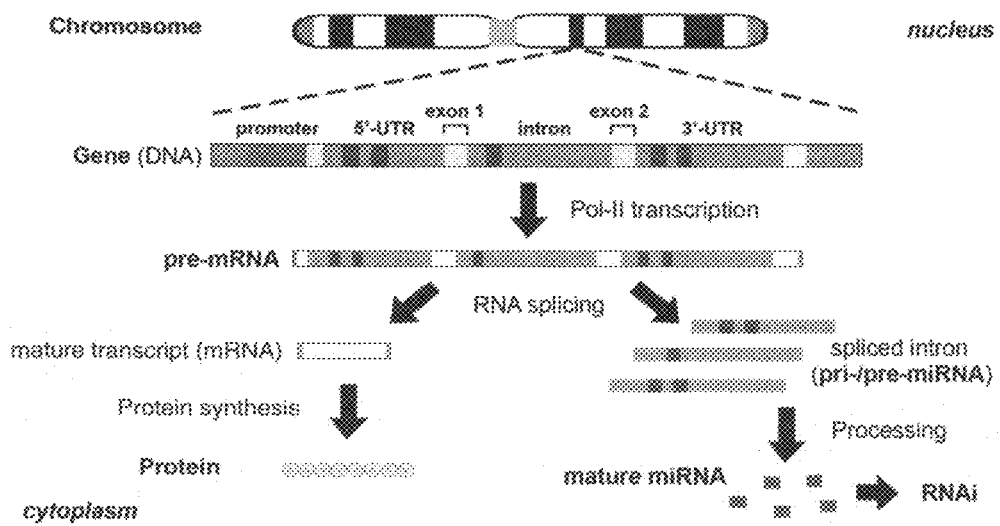

Referring particularly to the drawings for the purpose of illustration only and not limitation, there is illustrated:

FIG. 1 depicts the intracellular mechanism of natural intronic microRNA (miRNA) biogenesis.

Figure 2:
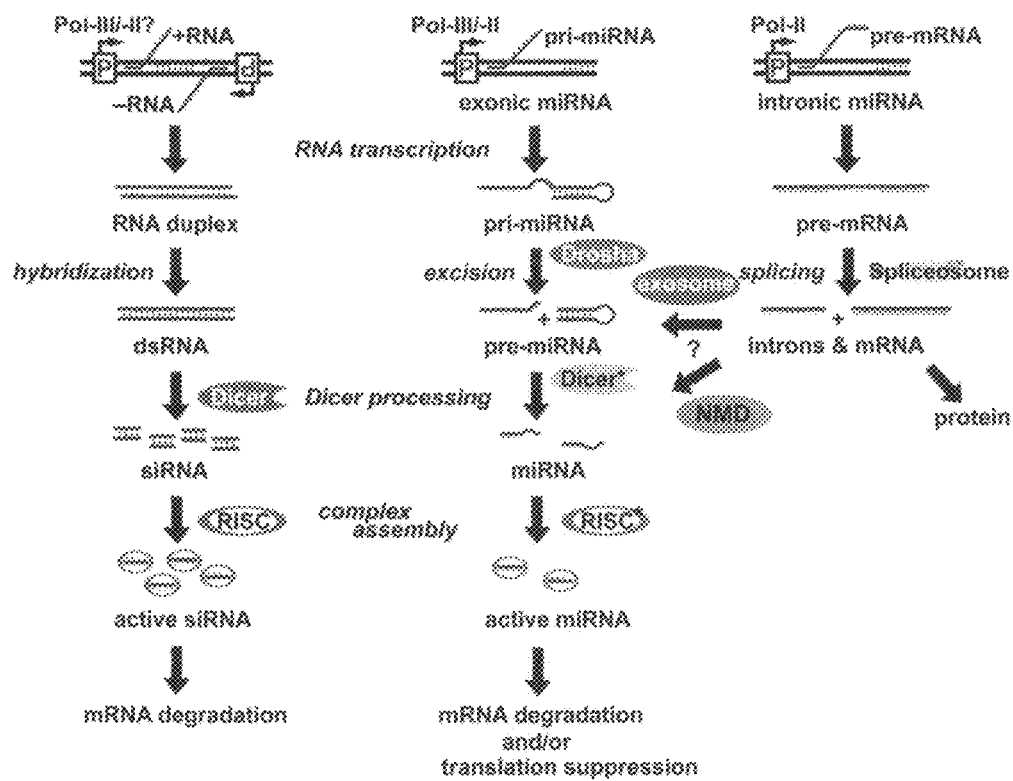

FIG. 2 depicts the different biogenesis mechanisms among the siRNA, exonic (intergenic) microRNA and intronic microRNA pathways.

FIGS. 3A-D depict the preferable embodiment of the SpRNAi-incorporated recombinant gene (SpRNAi-RGFP) construct in an expression-competent vector composition (A) (SEQ ID NO: 32), and the strategy (B) of using this composition to generate man-made microRNA, mimicking the biogenesis of the natural intronic miRNA. In vivo tests of an SpRNAi-RGFP expression composition directed against green EGFP in fish show an over 85% knockdown effect specifically on the targeted EGFP gene expression, as determined by Western blot analysis (C). The intron-derived anti-EGFP microRNA and its spliced precursor can be observed on a 1% formaldehyde agarose gel electrophoresis after Northern blot analysis (D).

FIGS. 4A-D show the assessment of different designs of intronic RNA inserts in the SpRNAi-RGFP construct. Effective miRNA biogenesis and its resulting gene silencing effect on a targeted green fluorescent protein (EGFP) gene are observed in two-week-old zebrafish larvae, demonstrating an asymmetric preference in RISC assembly between the transfection of [1] 5'-miRNA*-stemloop-miRNA-3' and that of [2] 5'-miRNA-stemloop-miRNA*-3' hairpin RNA structures, respectively (A). Gene silencing of EGFP is only observed in the transfection of the [2] pre-miRNA construct, but not the [1] construct. One example of an effective miRNA identity, miR-EGFP(280-302), is identified to be active in the transfection of the 5'-miRNA-stemloop-miRNA*-3' [2] construct (B). Since the color combination of EGFP and RGFP displays more red than green (as shown in deep orange), the expression level of target EGFP (green) is significantly reduced in the [2] pre-miRNA transfection, while vector indicator RGFP (red) is evenly present in all vector transfections (C)(SEQ ID NOS: 33-35). Western blot analysis of the EGFP protein levels confirms the specific silencing result of the [2] pre-miRNA transfection (D). No detectable gene silencing is observed in fish with other treatments, such as liposome only (Lipo), empty vector without any insert (Vctr), and siRNA (siR).

FIGS. 5A-C show the changes of cell morphology and cell proliferation after mir-302-like RNA molecules are transgenically expressed in human primary epithelial skin culture (hpESC), human prostatic carcinoma PC3 (PC3), and human primary melanoma culture Colo (Colo) cells. After the mir-302 transfection, the cells with positive mir-302 expression are named hpESC+mr-302, PC3+mir-302 and Colo+mir-302, respectively.

FIGS. 6A-E show the embryonic stem (ES) cell properties of the Colo and PC3 cells with transgenic mir-302 expression (e.g. Colo+mir-302 and PC3+mir-302), including formation of embryoid bodies (A), Western blotting of the positive Oct3/4, SSEA-3 and SSEA-4 marker expression (B), and assays of genomic demethylation (C), CpG demethylation (D) and cell migration (E).

Figure 7:
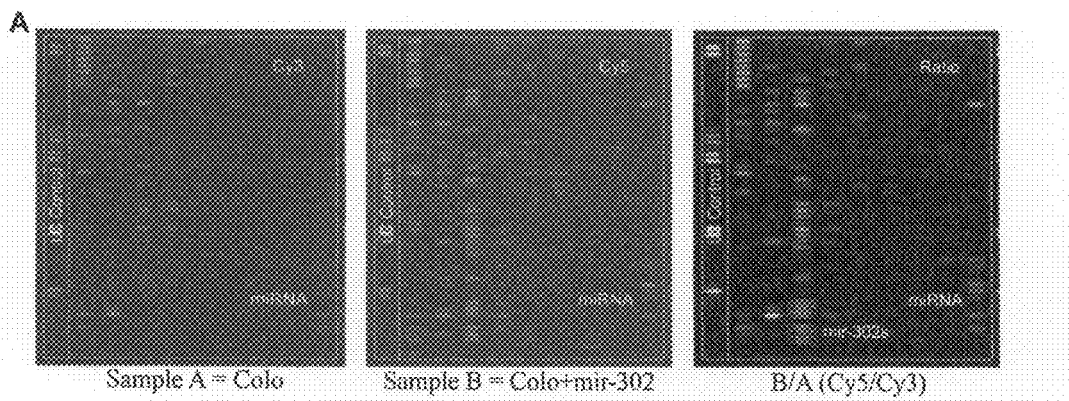

FIGS. 7A-B show the result of microRNA (miRNA) microarray analysis, confirming that the mir-302 familial members are all highly expressed in the SpRNAi-RGFP transfected Colo cells (namely Colo+mir-302).

Figure 8:
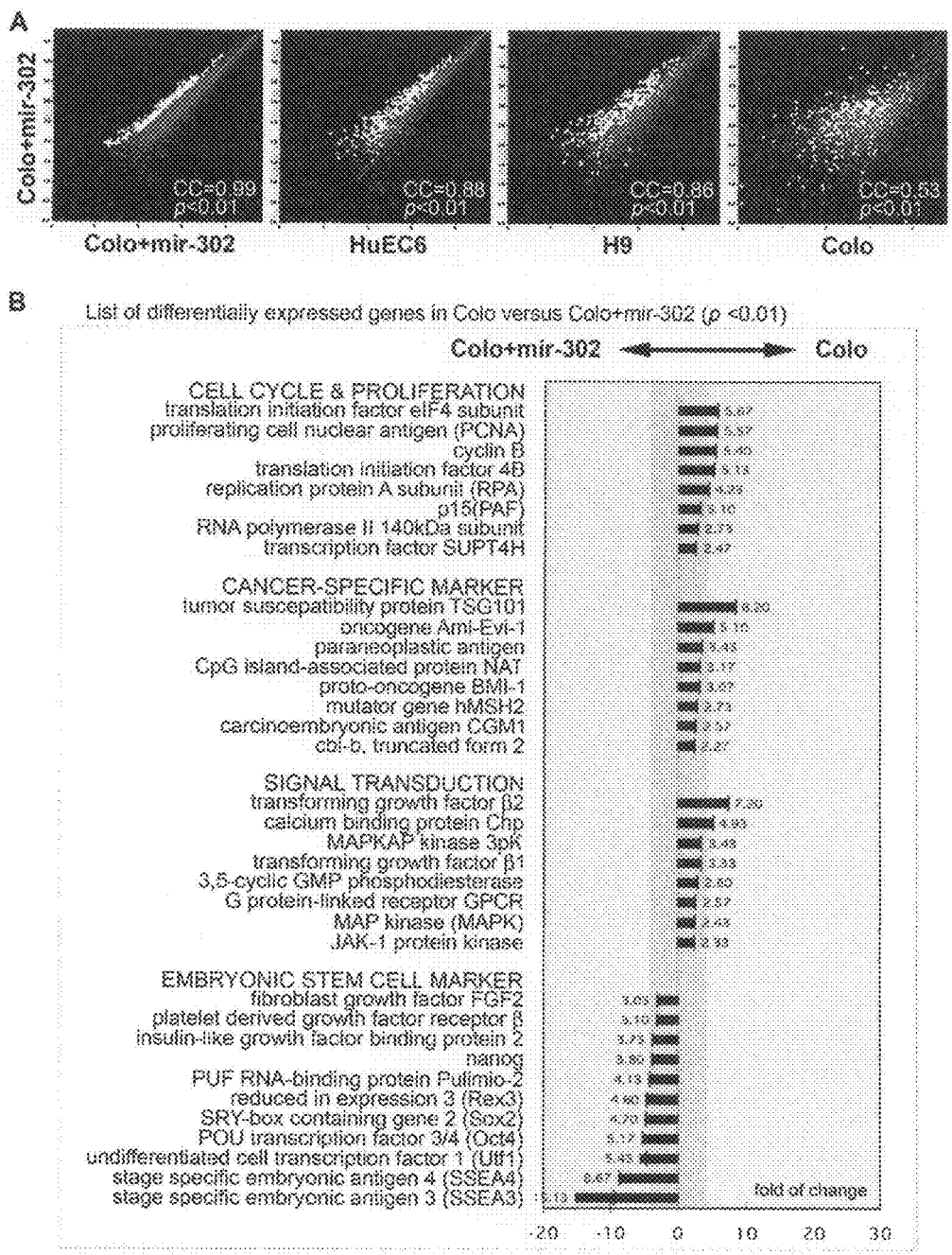

FIGS. 8A-B show the result of gene microarray analysis (Affymetrix human GeneChip U133A&B, CA) of altered gene expression in the Colo cells with transgenic mir-302 expression (Colo+mir-302), showing a significant increase of expression of many embryonic marker genes and a marked decrease of expression of cancer markers and developmental signal genes, which is very similar to the gene expression patterns of human embryonic stem HuEC8 and H9 cells.

Figure 9:
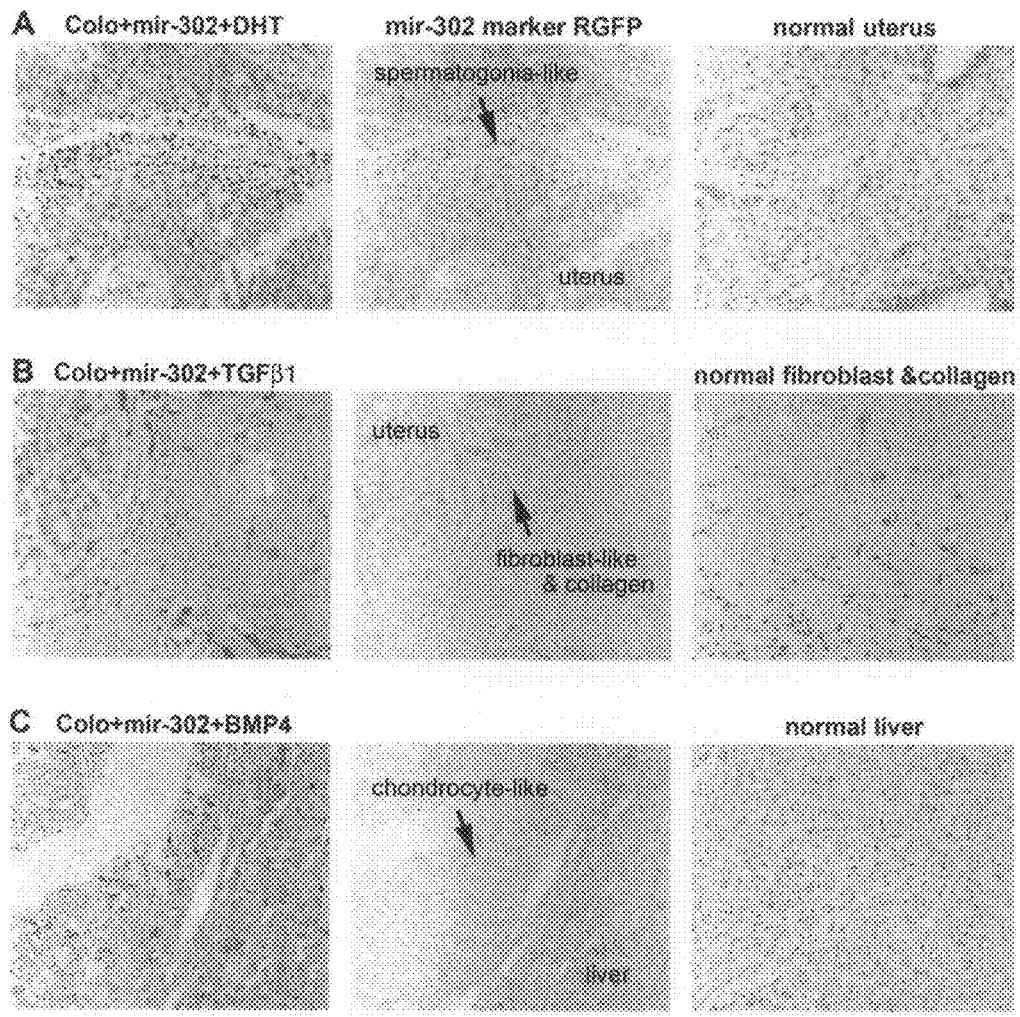

FIGS. 9A-C show that the transfected Colo cells expressing transgenic mir-302 (Colo+mir-302) with a red RGFP label can differentiate into various cell types, such as primordial chondrocytes, fibroblasts and even germ line cells, after treatments with different developmental signals (e.g. hormones and/or growth factors), demonstrating their pluripotent potentials similar to those of embryonic stem cells.

Figure 10:
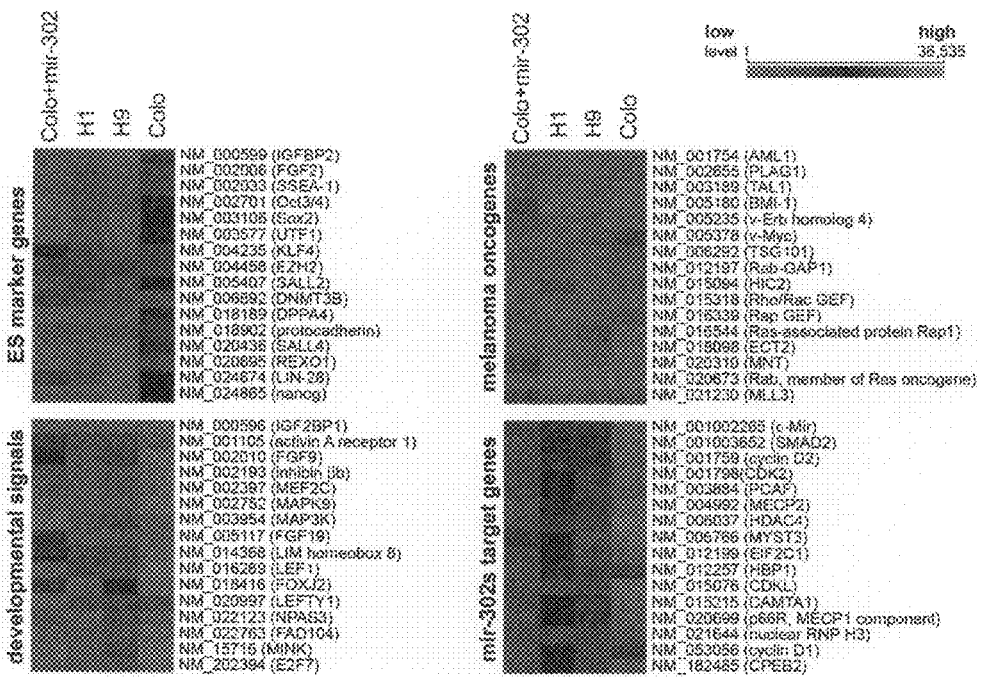

FIG. 10 is the data of the microarray analysis using new Affymetrix U133 plus 2 human genome genechips, showing that SSEA-1 is moderately expressed in the mir-302-induced ES-like Colo+mir-302 cells, whereas Klf4 is not expressed. Furthermore, many standard human ES cell markers are highly expressed in the transfected Colo+mir-302 cells but not original Colo cells, including Oct4, Sox2, Nanog, Utf1, Rex1, SALL2 and SALL4, confirming the result of FIG. 8B.

DETAILED DESCRIPTION OF THE INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 4:
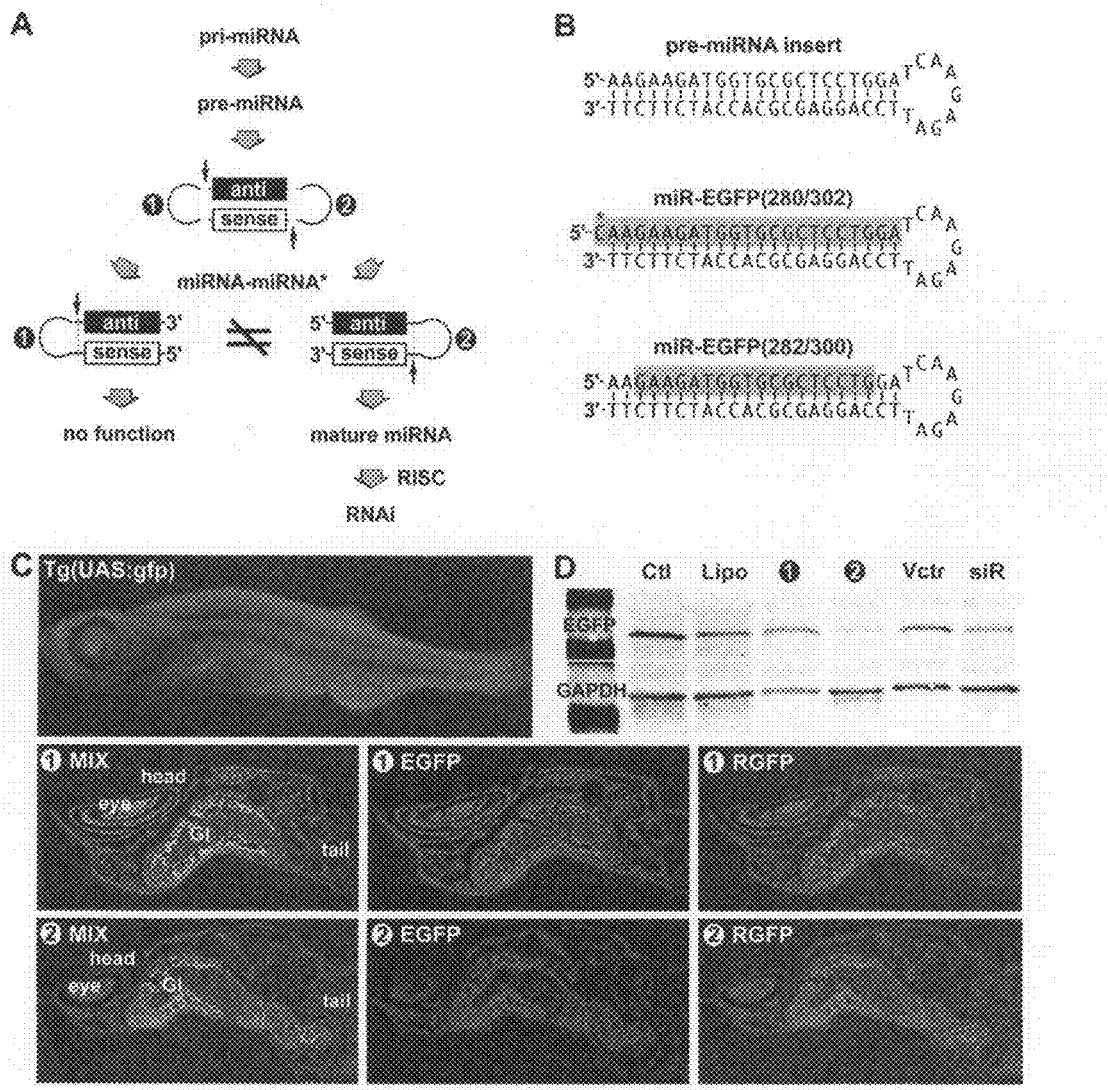
Figure 5:
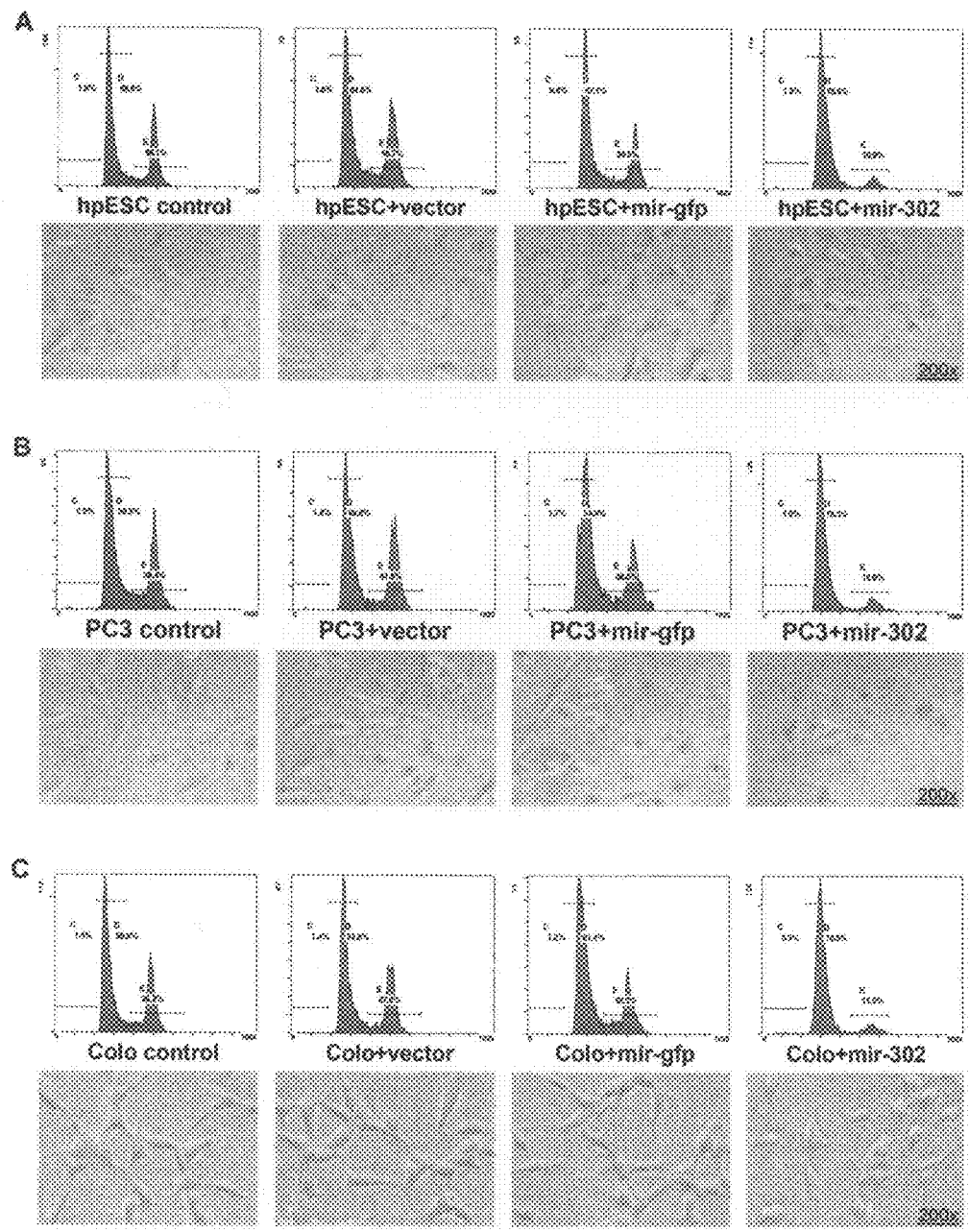

The present invention provides a novel composition and method for altering genetic characteristics of eukaryotic cells using intron-derived RNAs. Without being bound by any particular theory, such an alteration of genetic characteristics is directed to a newly discovered intron-driven gene silencing mechanism, triggered by transfection of a recombinant gene containing at least an RNA splicing-competent intron, namely SpRNAi, in the cell or organism of interest. SpRNAi further carries an intronic RNA insert, which can be released by intracellular RNA splicing and processing machineries and then triggers RNAi/PTGS-related gene silencing effects on target gene transcripts that contain high complementarity to the intronic RNA insert. Generally, as shown in FIG. 4 and FIG. 5, when the recombinant gene is chemically and/or liposomally transfected, or otherwise introduced by viral infection into the eukaryotic cells. The intronic RNA insert is co-transcribed with the recombinant gene by Pol-II and then released from the recombinant gene transcript by RNA splicing and processing mechanisms, such as spliceosomes, exosomes and nonsense-mediated decay (NMD) systems. During RNA splicing, the intronic RNA forms a lariat RNA and then further processed into gene silencing effectors, such as short-temporary RNA (stRNA), antisense RNA, small-interfering RNA (siRNA), short-hairpin RNA (shRNA), microRNA (miRNA), Piwi-interacting RNA (piRNA) and their precursor RNAs. Consequently, these gene silencing effectors either degrade their target gene transcripts or suppress target proteins' translation through the functional assembly, action of RNA-induced silencing complex (RISC) and RNAi-induced initiator of transcriptional silencing (RITS).

Mimicking the natural pre-mRNA splicing and processing mechanism, we use intracellular spliceosomal, exosomal and NMD system to catalyze the intron removal and processing of our invented SpRNAi-RGFP expression system. Through a sequential assembly of intracellular spliceosomal components on several snRNP-recognition elements of SpRNAi (e.g. binding sites for snRNPs U1, U2 and U4/U6.U5 tri-snRNP), SpRNAi is released and further processed into gene silencing effectors. The methods for incorporating the synthetic snRNP-recognition elements into SpRNAi and then incorporating such SpRNAi into the recombinant RGFP construct of the present invention are described in Examples 1 and 2, respectively.

Designs Construction and Assessment of a Pol-1'-Mediated Recombinant SpRNAi-RGFP Gene Expression System Capable of Inducing Intronic RNA-Mediated Gene Silencing Effects.

Strategy for triggering intracellular RNA splicing- and processing-directed gene silencing mechanism in vivo has been tested, using a Pol-II-transcribed recombinant gene vector of the present invention, namely SpRNAi-RGFP, which contains an artificial splicing-competent intron (SpRNAi) for expressing intronic gene silencing effectors (FIGS. 3A and B), such as miRNA and hairpin-like shRNA. Incorporation of SpRNAi into a red-shifted fluorescent protein gene (RGFP) is genetically engineered by sequential ligation of several synthetic DNA sequences as shown in Examples 1 and 2. SpRNAi comprises a precursor miRNA or shRNA insert, which can be released by intracellular RNA splicing and processing mechanisms, such as spliceosomes, exosomes and NMD system components, then triggers an intronic RNA-mediated gene silencing mechanism through the generation of mature miRNA or shRNA gene silencing effectors. Although we show here a model of inducing target gene silencing through the intracellular RNA splicing and processing of the recombinant gene transcripts or constructs, the same principle can be also used to design and produce gene silencing effectors functioning via the RNA processing of ribosomal precursor RNA (pre-rRNA), which is mainly transcribed by type-I RNA polymerases (Pol-I). Other RNA transcripts capable of being used to carry and generate SpRNAi include hnRNA, rRNA, tRNA, snoRNA, snRNA, viral RNA, pre-microRNA, mRNA and their precursors as well as derivatives.

Figure 3:
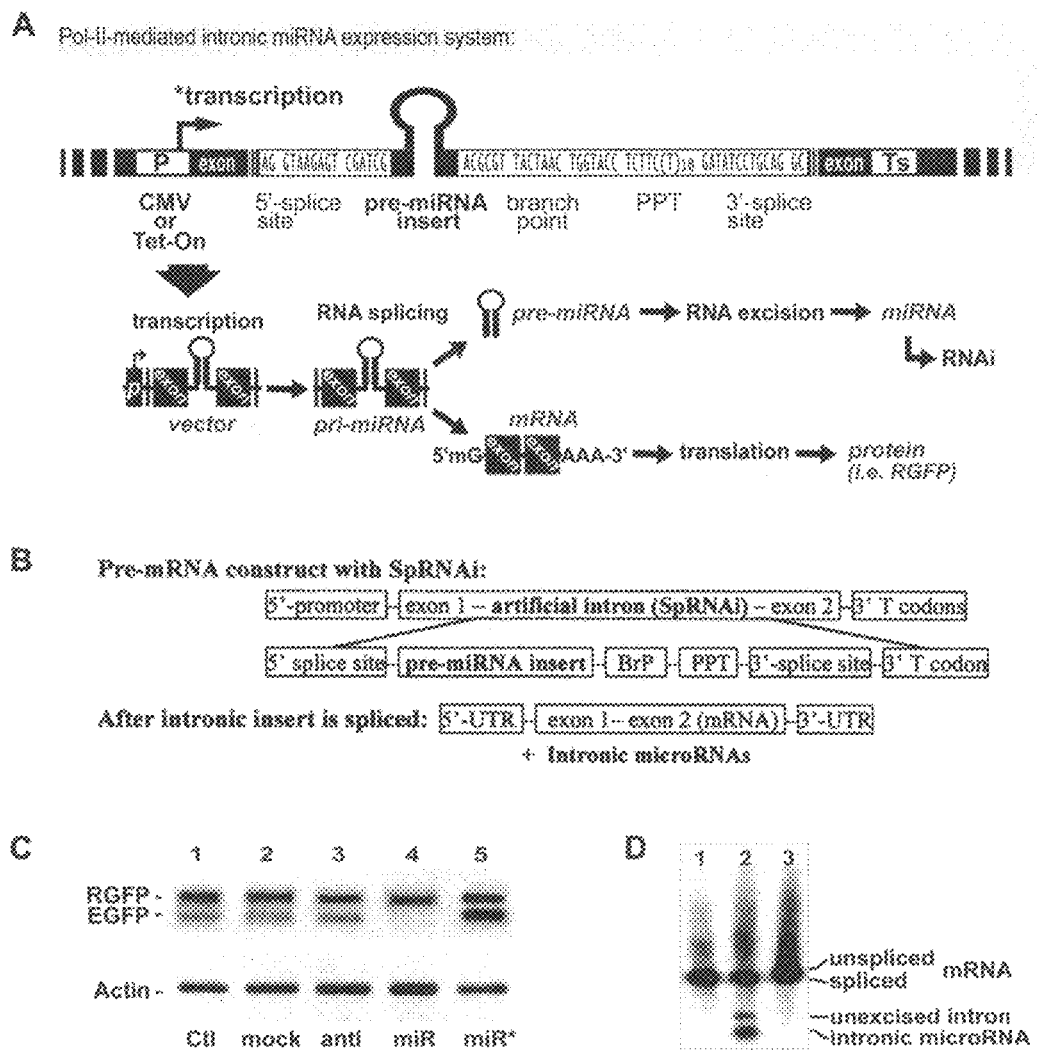

As shown in Examples 1-2 and FIG. 3A, SpRNAi was synthesized and incorporated into an intron-free red-shifted fluorescent protein gene (RGFP or rGFP), which was mutated from the HcRed1 chromoproteins of *Heteractis crispa*. Because the inserted SpRNAi disrupted the functional fluorescent protein structure of RGFP, we were able to check the intron removal and mRNA maturation of RGFP gene transcripts through the reappearance of red fluorescent light emission at the 570-nm wavelength in a successfully transfected cell or organism. Construction of this recombinant SpRNAi-RGFP construct was based on the natural structures of a spliceosomal intron in a precursor messenger RNA (pre-mRNA). The major components of SpRNAi include several snRNP recognition sites and linkers, such as 5'- and 3'-splice sites in the ends for precise cleavage, a branch point motif (BrP) for splicing recognition, a polypyrimidine tract (PPT) for spliceosomal interaction, linkers for connection of each of these components and some restriction sites for desired intronic insertion. Structurally from the 5' to 3' end as shown in FIG. 3B, SpRNAi of the present invention contains a 5'-splice site, an anti-(target gene) intronic insert, which can be spliced and processed to form gene silencing effectors such as a mir-302-like gene silencing effector), a branch point motif (BrP), a polypyrimidine tract (PPT), and a 3'-splice site for functional spliceosome assembly. In addition, some translational termination codons (T codon) may be located in the linker sequences close to the 3'-splice site of SpRNAi.

Generically, the 5'-splice site is a nucleotide sequence containing or homologous to either 5'-GTAAGAGK-3' (SEQ. ID. NO. 4) or GU(A/G)AGU motifs (such as 5'-GTAAGAGGAT-3'(SEQ ID NO: 30), 5'-GTAAGAGT-3', 5'-GTAGAGT-3' and 5'-GTAAGT-3'), while the 3'-splice site is a nucleotide sequence containing or homologous to either GWKSCYRCAG (SEQ. ID. NO. 5) or CT(A/G)A(C/T)NG motifs (such as 5'-GATATCCTGC AG-3'(SEQ ID NO: 31), 5'-GGCTGCAG-3' and 5'-CCACAG-3'). Moreover, a branch point sequence is located between the 5'- and 3'-splice sites, containing homology to 5'-TACTWAY-3' (SEQ. ID. NO. 6) motifs, such as 5'-TACTAAC-3' and 5'-TACTTAT-3'. The adenosine "A" nucleotide of the branch-point sequence forms a part of (2'-5')-linked lariat intron RNA by cellular (2'-5')-oligoadenylate synthetases and spliceosomes in almost all spliceosomal introns. Furthermore, a poly-pyrimidine tract is closely located between the branch-point and 3'-splice site, containing a high T or C content oligonucleotide sequence homologous to either 5'-(TY)m(C/-)(T)nS(C/-)-3' (SEQ. ID. NO. 7) or 5'-(TC) nNCTAG(G/-)-3' (SEQ. ID. NO. 8) motifs. The symbols of "m" and "n" indicate multiple repeats ≥1; most preferably, the m number is equal to 1~3 and the n number is equal to 7~12. The symbol "-" refers an empty nucleotide in the sequence. There are also some linker nucleotide sequences for the connection of all these intron components. Based on the guideline of 37 CFR 1.822 for symbols and format to be used for nucleotide and/or amino acid sequence data, the symbol W refers to an adenine (A) or thymine (T)/uracil (U), the symbol K refers to a guanine (G) or thymine (T)/uracil (U), the symbol S refers to a cytosine (C) or guanine (G), the symbol Y refers to a cytosine (C) or thymine (T)/uracil (U), the symbol R refers to an adenine (A) or guanine (G), and the symbol N refers to an adenine (A), cytosine (C), guanine (G) or thymine (T)/uracil (U)." For all of the above spliceosomal recognition components, the deoxythymidine (T) nucleotide is replaceable with uridine (U).

To test the function of a spliced SpRNAi insert, various oligonucleotide agents can be cloned into the anti-(target gene) intronic insert site of the recombinant SpRNAi-RGFP construct. The anti-(target gene) intronic insert site contains multiple restriction and cloning sites, which are recognized by restriction enzymes selected from the group of AatII, AccI, AflII/III, AgeI, ApaI/LI, AseI, Asp718I, BamHI, BbeI, BclI/II, BglII, BsmI, Bsp120I, BspHI/LU11I/120I, BsrI/BI/GI, BssHII/SI, BstBI/U1/XI, ClaI, Csp6I, DpnI, DraI/II, EagI, EclI36II, EcoRI/RII/47III, EheI, FspI, HaeIII, HhaI, HinPI, HindIII, HinfI, HpaI/II, KasI, KpnI, MaeII/III, MfeI, MluI, MscI, MseI, NaeI, NarI, NcoI, NdeI, NgoMI, NotI, NruI, NsiI, PmlI, Ppu10I, PstI, PvuI/II, RsaI, SacI/II, SalI, Sau3AI, SmaI, SnaBI, SphI, SspI StuI, TaiI, TaqI, XbaI, XhoI, XmaI endonuclease and the combination thereof. These intronic oligonucleotide inserts are DNA templates that can be transcribed as highly secondary structures selected from the group consisting of lariat-form RNA, short-temporary RNA (stRNA), antisense RNA, small-interfering RNA (siRNA), double-stranded RNA (dsRNA), short-hairpin RNA (shRNA), microRNA (miRNA), Piwi-interacting RNA (piRNA), ribozyme, and their precursors as well as derivatives in either sense or antisense conformation, or both, and a combination thereof.

For the convenience of gene delivery and activation in the cell or organism of interest, the recombinant SpRNAi-RGFP construct of the present invention is preferably incorporated into an expression-competent vector, selected from the group consisting of DNA transgene, plasmid, retrotransposon, transposon, jumping gene, viral vector, and a combination thereof. Such vector so obtained is introduced into the cell or organism by a high efficient gene delivery method selected from the group consisting of chemical/liposomal transfection, electroporation, transposon-mediated DNA recombination, jumping gene insertion, viral infection, micro-injection, gene-gun penetration, and a combination thereof. The vector may further contain at least a viral, Pol-II, or Pol-III promoter, or a combination thereof, for expressing SpRNAi-RGFP construct. Moreover, the vector may contain a Kozak consensus translation initiation site to increase translation efficiency in eukaryotic cells, multiple SV40 polyadenylation signals downstream of SpRNAi-RGFP construct for processing the 3'-end of the recombinant gene transcript, a pUC origin of replication for propagation in prokaryotic cells, at least two restriction sites for incorporation of SpRNAi-RGFP construct into the vector, an optional SV40 origin for replication in mammalian cells that express the SV40 T antigen, and an optional SV40 early promoter for expressing antibiotic resistance gene in replication-competent prokaryotic cells. The expression of antibiotic resistance genes is used to serve as a selective marker for searching of successfully transfected or infected clones, possessing resistance to the antibiotics selected from the group consisted of penicillin G, ampicillin, neomycin, paromycin, kanamycin, streptomycin, erythromycin, spectromycin, phophomycin, tetracycline, rifapicin, amphotericin B, gentamycin, chloramphenicol, cephalothin, tylosin, and a combination thereof.

SpRNAi-RGFP vector so obtained has been tested in a Tg(actin-GAL4:USA-gfp) strain zebrafish in vivo to target against its green EGFP gene expression. As shown in Examples 3 and 6 as well as FIG. 3C, the liposomal transfection of an anti-EGFP pre-miRNA insert in SpRNAi-RGFP plasmid (lane 4) presents a very strong EGFP gene silencing effect (>80% gene knockdown), whereas no silencing effect can be detected in those of other inserts indicated by lanes from left to right: 1, blank vector control (Ctl); 2, pre-miRNA insert targeting HIV-p24 (mock); 3, antisense EGFP insert without the hairpin loop structure (anti); and 5, reverse pre-miRNA sequence which is completely complementary to the anti-EGFP pre-miRNA (miR*). No such effect was detected on off-target genes, such as marker RGFP and house-keeping β-actin, suggesting that such intronic miRNA-mediated RNA interference (RNAi) is highly target-specific. Further, by Northern blotting analysis (FIG. 3D), we have observed the generation and release of small effective intronic RNAs only from the designed SpRNAi-RGFP gene transcript (middle lane 2), but not from a natural transcript of the intron-free RGFP (left lane 1) or a transcript of a defective SpRNAi-RGFP construct without a functional 5'-splice site, while spliced RGFP exons can be linked together to form mature RNA for functional red fluorescent protein synthesis.

Optimization of Effective Intronic microRNA (miRNA) Designs

The above and foregoing experiments establish the fact that intronic miRNAs provide effective means and method for silencing target gene expression in vivo. We first assess the efficacy of the intronic miRNA-mediated gene silencing and then determine the best structural designs for the intronic pre-miRNA inserts capable of inducing an optimal gene silencing effect. Based on these studies, we have learned that a strong structural preference presents in the selection of a mature miRNA strand for intracellular assembly of the RNAi-related gene silencing mechanism, RNA-induced gene silencing complex (RISC). RISC is a protein-RNA complex that directs either target gene transcript degradation or translational repression of the target gene transcript through a RNA interference (RNAi) or post-transcriptional gene silencing (PTGS) mechanism.

In zebrafish, we have observed that the stem-loop structure of pre-miRNA determines the sequence of mature miRNA for RISC assembly, which is different from the known siRNA-associated RISC assembly (Lin et. al. (2005) Gene 356: 32-38). Formation of siRNA duplexes plays a key role in assembly of the siRNA-associated RISC. The two strands of the siRNA duplex are functionally asymmetric, but assembly into the RISC complex is preferential for only one strand. Such a preference is determined by the thermodynamic stability of each 5'-end base-pairing in the siRNA duplex strand. Based on this siRNA model, the formation of miRNA and its complementary miRNA (miRNA*) duplex was thought to be an essential step for the assembly of miRNA-associated RISC. If this were true, no functional bias would be observed in the stem-loop structure of a pre-miRNA. However, we observed that the stem-loop of the intronic pre-miRNA was involved in the strand selection of a mature miRNA for intracellular RISC assembly.

In experiments, we constructed anti-EGFP miRNA-expressing SpRNAi-RGFP vectors, as described in Examples 1 and 2, and two symmetric pre-miRNAs, miRNA-stem-loop-miRNA* [1] and miRNA*-stemloop-miRNA [2], were synthesized by a DNA synthesizer machine and inserted into the pre-made recombinant SpRNAi-RGFP vectors, respectively. Both pre-miRNA constructs contained the same double-strandstem-arm region, which was directed against the EGFP nucleotide 280-302 sequence. Because the intronic insert site of SpRNAi-RGFP construct is flanked with a PvuI and an MluI restriction site at its 5'- and 3'-ends, respectively, the primary insert can be easily removed and replaced by various anti-gene inserts (e.g. anti-EGFP or mir-302 pre-miRNA) possessing cohesive ends. By allowing changes in the insert of SpRNAi directed against different gene transcripts, this intronic miRNA expression system provides a valuable tool for developing miRNA-associated genetic applications in vivo.

To determine the structural preference of the designed pre-miRNA, we isolated the zebrafish small RNAs by mirVana miRNA isolation filter columns (Ambion, Austin, Tex.) and then precipitated all potential miRNA sequences complementary to the targeted EGFP by latex beads containing the target sequence. One full-length miRNA, miR-EGFP(280-302), was verified to be active in the transfections of the 5'-miRNA-stemloop-miRNA*-3' [2] construct, as shown in FIGS. 4A and 4B (gray-shading sequences). Because this effective mature miRNA was detected only in the zebrafish transfected by the 5'-miRNA-stemloop-miRNA*-3' construct [2], the miRNA-associated RISC tended to preferably interact with the construct [2] rather than the [1] pre-miRNA structure. For visual display of the correlation between targeted gene silencing and miRNA expression (FIG. 4C), we used a Tg(actin-GAL4:UAS-gfp) strain zebrafish, which constitutively expressed a green fluorescent EGFP protein driven by a universal β-actin promoter located in almost all cells of the zebrafish, while the transfection of the anti-EGFP SpRNAi-RGFP gene vector into the zebrafish co-expressed a red fluorescent protein RGFP, serving as a positive marker indicator for miRNA generation in the affected cells. After applied SpRNAi-RGFP vector encapsulated by a FuGene cationic liposomal reagent (Roche, IN) to the fish embryos, we found that all tested vectors completely penetrated the zebrafish within 24 hours, providing fully; systemic delivery of the vectors except for the scales and bones.

The marker RGFP (red) was detected in all vector-transfected zebrafish, whereas the silencing of target EGFP expression (green) was observed only in the fish transfected by the 5'-miRNA-stemloop-miRNA*-3' [2] pre-miRNA. As shown in FIG. 4D, Western blot analysis quantitatively confirmed this gene silencing result, demonstrating a >85% RGFP knockdown in the construct [2]-transfected zebrafish. The gene silencing effect in gastrointestinal (GI) tract area was however lower that other tissues, probably due to a high RNase activity in this area. Because the same 5'-end thermostability is applied to both anti-EGFP pre-miRNA stem-arms, we suggest that the stem-loop structure of pre-miRNA is involved in the strand selection of mature miRNA for functional RISC assembly. Given that the cleavage site of Dicer in the stem-arm is known to determine the strand selection of mature miRNA, the stem-loop of a pre-miRNA may function as a determinant for the recognition of the special cleavage site. Therefore, based the broad heterogeneity of natural stem-loop structures among various native miRNA species, we selectively used a pair of manually improved pre-mir-302 loops in these experiments, such as 5'-GCTAAGCCAGGC-3' (SEQ. ID. NO. 1) and 5'-GCCTG-GCTTAGC-3' (SEQ. ID. NO. 2), which have been tested to provide an optimal RISC assembly effect for the present invention.

SpRNAi-RGFP-Mediated mir-302 Transfection in Human Primary Epithelial Skin Culture (hpESC), Human Prostatic Carcinoma PC3 (PC3), and Human Primary Melanoma Culture Colo (Colo) Cells Based on the above studies, we have designed and tested an optimal SpRNAi-RGFP construct with either a manually linked mir-302a-mir-302b-mir-302c-mir-302d pre-miRNA cluster insert or a manually re-designed mir-302 pre-miRNA insert (e.g. a hairpin-like sequence containing 5'-UAAGUGCUUC CAUGUUUUAG UGU-3' (SEQ. ID. NO. 9)) for transfectively silencing the developmental and differentiation-related target genes in tested hpESC, PC3 and Colo cells. The mature sequences of mir-302a, mir-302b, mir-302c and mir-302d are 5'-UAAGUGCUUC CAUGUUUUGG UGA-3' (SEQ. ID. NO. 10), 5'-UAAGUGC-UUC CAUGUUUUAG UAG-3' (SEQ. ID. NO. 11), 5'-UAAGUGCUUC CAUGUUUCAG UGG-3' (SEQ. ID. NO. 12), and 5'-UAAGUGCUUC CAUGUUUGAG UGU-3' (SEQ. ID. NO. 13), respectively. These mir-302-like gene-silencing effecter homologues share a highly conserved 5'-end region in their first seventeenth nucleotides (100% homology), identical to 5'-UAAGUGCUUC CAU-GUUU-3' (SEQ. ID. NO. 3). In these mir-302 homologous sequences, thymine (T) can be used in place of uracil (U).

In these experiments, we transgenically transfect the mir-302a-mir-302b-mir-302c-mir-302d pre-miRNA cluster into hpESC and PC3 cells, and the re-designed mir-302 homologue (SEQ. ID. NO. 9) into Colo cells, respectively. After mir-302 transfection, all these cell lines transform their morphology (lower panels) from spindle or amoeba-like shapes to a more round shape outline, indicating that they may lose ability for cell migration and have a very slow cell replication rate similar to stem cell growth (FIGS. 5A-C). Flow cytometry analyses (upper panels) of their DNA contents (y axis) to different cell cycle stages (x axis) show an over 67% reduction in the mitotic cell population, confirming the slow cell proliferation of these mir-302-transfected cells, while the cell population is indicated by the DNA content measured at each cell cycle stage. The first (left) and second (right) peaks represent the levels of resting G0/G1 and mitotic M phase cell populations in the entire tested cell population, respectively. The mitotic cell population is decreased from 36.1% to 10.9% in hpESC, from 38.4% to 12.6% in PC3, and from 36.5% to 11.5% in Colo cells after mir-302 transfection, whereas there is no significant changes in either cell morphology or cell proliferation after transfection with empty SpRNAi-RGFP vector or vector containing mir-gfp pre-miRNA insert. The mir-gfp pre-miRNA is designed to target against a firefly EGFP gene, which shares no homology to human and mouse genes. Based on these findings, we show that transgenic expression of mir-302 homologues can transform human primary culture cells and cancerous cells into a more embryonic stem (ES)-like morphology and rate of replication, similar to the changes observed in previously reported iPS cells (Okita et al., (2007) Nature 448: 313-317; Wernig et al., (2007) Nature 448: 318-324).

Assessment of Embryoid Body Formation, Embryonic Stem Cell Marker Expression, Genomic DNA Demethylation, and Reduction of Cell Migration in Colo and PC3 Cells with Transgenic mir-302 Expression (Namely Colo+mir-302 and PC3+mir-302)

Figure 6:
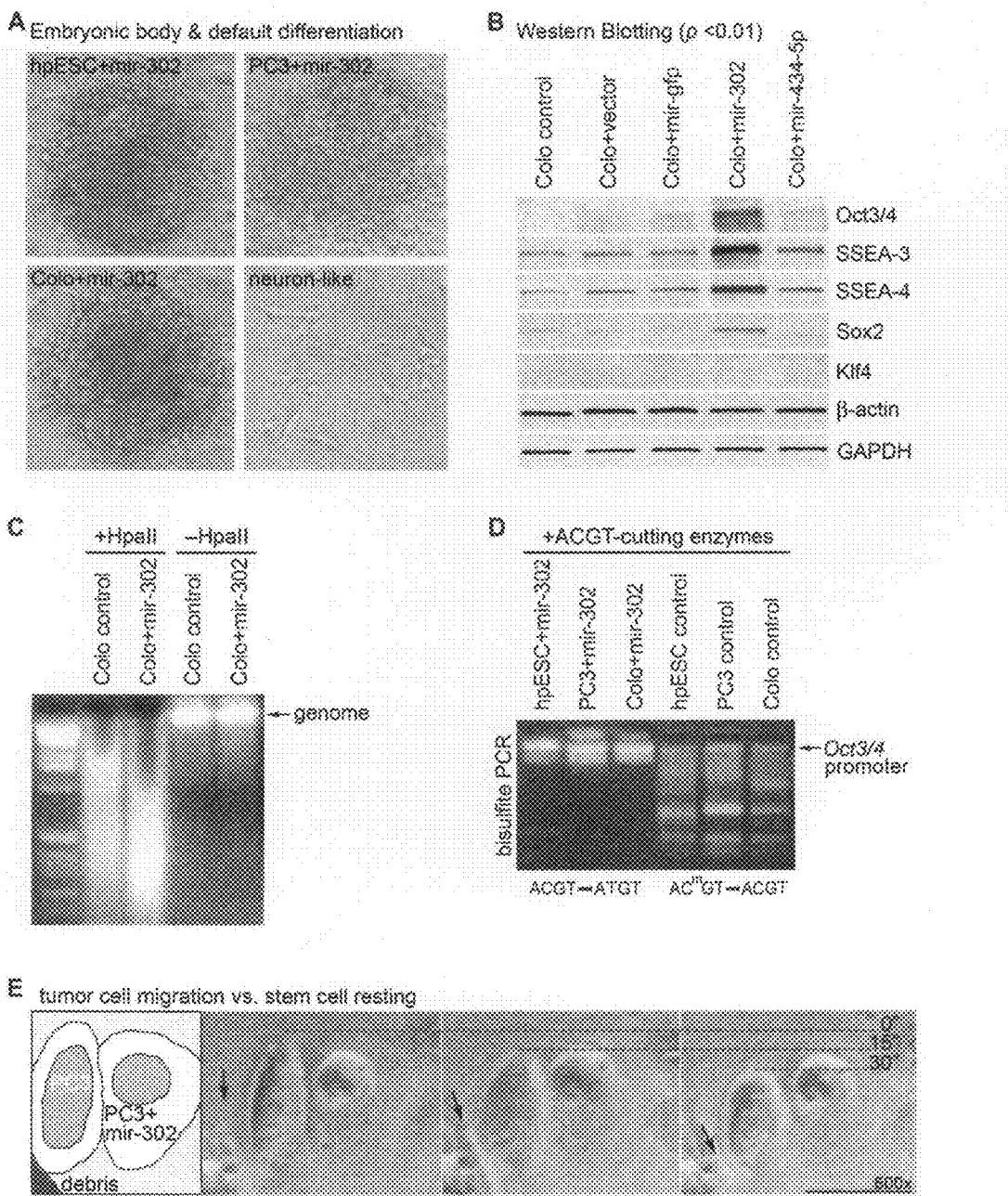

To further test the embryonic stem (ES)-like properties of the mir-302-transfected cells, we evaluate their embryoid body formation, ES marker gene expression, genomic demethylation, and reduction of cell migration. With very high-density cell culture confluence (>85%-90%), mir-302-transfected cells tended to form compact colonies reminiscent of embryoid bodies (EB) as well as the EB derived from native human ES cells (FIG. 6A). However, in the absence of proper guidance by any hormone or growth factor, these EB-like bodies would fall apart and differentiate into neuron-like primordial cells during subculturing (bottom right). To test the genetic properties of these ES- and EB-like cell types, we further evaluated their ES marker gene expression. For example, as shown in FIG. 6B, the Colo cells with transgenic mir-302 transfection (Colo+mir-302) strongly display a full category of standard ES cell markers, such as Oct3/4, SSEA-3, SSEA-4 and even Sox2, whereas no ES cell markers are detected in the control Colo cells and the Colo cells transfected with an empty SpRNAi-RGFP vector (Colo+vector), a vector expressing mir-gfp miRNA (Colo+mir-gfp), or a vector expressing native mir-434-5p miRNA (Colo+mir-434-5p). The mir-434-5p does not share any homologous target gene sequences with mir-302s. Since Colo is a differentiated human melanoma cell line, this result shows that the SpRNAi-RGFP-mediated mir-302 transfection is able to reprogram the Colo cells into an ES-like state, which is very similar to those in embryonic stem cells.

Oct3/4 (also termed Oct-3 or Oct-4) is one of the POU transcription factors, which is mainly and highly expressed in totipotent embryonic stem and germ cells (Scholer et al., (1989) EMBO J. 8: 2543-2550; Rosner et al., (1990) Nature 345: 686-692). A critical level of Oct3/4 expression is required to maintain stem cell self-renewal and pluripotency. Down-regulation of Oct3/4 results in differentiation of embryonic stem cells into divergent developmental programs. SSEA proteins, SSEA-1, -3 and -4, are originally identified by monoclonal antibodies recognizing lacto- and globo-glycolipids on the surface of pre-implantation-stage murine embryos and teratocarcinoma stem cells, but not on their differentiated derivatives (Solter et al., (1978) Proc. Natl. Acad. Sci. USA 75: 5565-5569). Undifferentiated primate embryonic stem (ES) cells, human embryonic cancer (hEC) and ES cells all express SSEA-3 and SSEA-4, but not SSEA-1 (Thomson et al., (1998) Science 282: 1145-1147). SSEA-3 and SSEA-4 are synthesized during oogenesis and mainly presented in the membranes of oocytes, zygotes and early cleavage-stage embryos (Shevinsky et al., (1982) Cell 30: 697-705). Sox2 functions as a core transcription factor in maintaining pluripotency, but this function is not specific to embryonic stem cells (Boyer et al., (2005) Cell 122: 947-956). Therefore, based on the current understanding of these embryonic stem cell markers, the Colo+mir-302 cells carry all characteristics and relative functions of these ES markers.

Change of epigenetic modification is another unique feature of pluripotent stem cells, particularly genomic demethylation (Hochedlinger et al., (2006) Nature 441: 1061-1067). In order to reprogram a differentiated somatic cell into an ES state, many embryonic genes need to be re-activated so as to inhibit developmental and differentiation-related signals or genes. DNA methylation plays a key role in regulating on and off switch of these genes. Because methylation in the upstream promoter region usually interferes with the assembly of transcriptional machinery essential for gene expression, a demethylation process must occur in order to re-activate the embryonic genes, such as Oct3/4, SSEA-3, SSEA-4 and Sox2. To assess the DNA methylation status of the Colo versus Colo+mir-302 cells, we first isolate the cell genomes (DNA isolation kit, Roche, IN) and perform genome digestion with a CCGG-cutting restriction enzyme HpaII, which is sensitive to CpG methylation and cleaves only an unmethylated CCGG site, but not a methylated CCGG site. FIG. 6C shows that the digested genome fragments of the Colo cell control is much larger than those of ES-like Colo+mir-302 cells, indicating that a highly demethylation status indeed occurs in the mir-302-transfected Colo cells. The original sizes of Colo and Colo+mir-302 genomes are almost identical.

FIG. 6D further shows the changes of methylation patterns of the Oct3/4 gene promoter region in the control hpESC, PC3 and Cole cells compared to their mir-302 transfected cells. To determine the methylation sites in this region, we treat the isolated genomic DNA with bisulfite (CpGenome DNA modification kit, Chemicon, CA), which converts all unmethylated cytosine to uracil, and then isolate the Oc3/4 5'-upstream promoter region using polymerase chain reaction (long template PCR extension kit, Roche, IN) with two forward primers 5'-GTTGTTTTGT TTTG-GTTTTG GATAT-3' (SEQ ID NO: 36) and 5'-ATTGTTTT-GTTTTGGTTTG GATTTA-3' (SEQ ID NO: 37) and one reverse primer 5'-GTAGAAGTGC CTCTGCCTTC C-3' (SEQ ID NO: 38). The cell genomes (100 ng) are first mixed with the primers (total 150 pmole) in 1×PCR buffer, heated to 94° C. for 4 min, and immediately cooled on ice. Then, 25 cycles of PCR are performed as follows: 92° C. for 1 min, 55° C. for 1 min and then 70° C. for 5 min. After that, the PCR products are collected by a PCR purification kit (Qiagen, CA) and digested with an equal mixture (5 U each) of multiple ACGT-cutting restriction enzymes, containing AclI (AACGTT), BmgBI (CACGTC), PmlI (CACGTG), SnaBI (TACGTA) and HpyCH41V (ACGT). Because the unmethylated ACGT sites in this region are changed into AUGT sites by bisulfite, which cannot be cleaved by the above restriction enzyme mixture, the result of FIG. 6D demonstrates that at least four methylated ACGT sites in the control hpESC, PC3 and Cole cells are reprogrammed to become demethylated in the mir-302 transfected cells. This mir-302-mediated demethylation of the Oct3/4 gene promoter region may also contribute to the re-activation of Oc3/4 gene expression in the mir-302 transfected cells, such as Colo+mir-302.

In addition, reduction of cell migration is often observed in the mir-302 transfected cancerous cells, such as PC3 and Colo cell lines. Given that embryonic stem cells tend to rest in one place and form an embryoid body in situ, this may explain why the PC3 and Colo cells lose their migration capability after the mir-302 transfection. As shown in FIG. 6E, when placing a PC3 cell next to a PC3+mir-302 cell, we can clearly observe that the cancerous PC3 cell quickly migrates along one side of the PC3+mir-302 cell in just 30 seconds. Black arrows indicate the direction of PC3 cell movement. This result suggests a potential therapeutical application for the mir-302 transfection in cancer cells, which may not only reprogram the cancer cells into useful stem cells but also reduce the chance of cancer metastasis. More advantageously, since the mir-302-transfected cancerous cells are still immune-compatible to the patients, the ES-like pluripotent cells so obtained can be used for transplantation therapy without the risk of immune rejection.

Identification of Transgenic mir-302 Expression Using miRNA Microarray Analysis

To confirm the transgenic mir-302 expression in the transfected cells, we perform microRNA (miRNA) microarray analysis. At 70% confluency, small RNAs from each cell line are isolated using a mirVana™ miRNA isolation kit (Ambion, Inc., Austin, Tex.), following the manufacturer's suggestion. The purity and quantity of the isolated small RNAs are assessed using 1% formaldehyde-agarose gel electrophoresis as well as spectrophotometer measurement (Bio-Rad, Hercules, Calif.) and then submitted to LC Sciences (San Diego, Calif.) for miRNA microarray analysis. In the Cy3 and Cy5 intensity images, as signal intensity increases from level 1 to level 65,535 the corresponding color changes from blue to green, to yellow, and to red. In the Cy5/Cy3 ratio image, when Cy3 level is higher than Cy5 level the color is green; when Cy3 level is equal to Cy5 level the color is yellow; and when Cy5 level is higher than Cy3 level the color is red. As shown in FIG. 7A, Cy3 refers to cells without any treatment (i.e. Colo) while Cy5 refers to cells with the transgenic mir-302 transfection (i.e. Colo+mir-302). In the Cy5/Cy3 ratio image (most right), all native mir-302 familial members (white circles) are highly expressed after SpRNAi-RGFP-mediated mir-302 transfection. Because the mir-302 familial members and our re-designed mir-302 agents share over about 91% homology, this result indicates that the re-designed mir-302 agents can act as a mir-302 member and replace the function of native mir-302s. FIG. 7B shows the detailed list of differentially expressed miRNAs in Colo+mir-302 cells.

Based on the result of FIG. 7A, we also found that the elevation of mir-302 expression can further increase the expression of native mir-302s and some other microRNAs, such as mir-92, mir-93, mir-200c, mir-367, mir-371, mir-372, mir-373, mir-374, and the whole mir-520 familial members. Analysis of their target genes using the miRBase:: Sequences program (http://microrna.sanger.ac.uk/) demonstrated that mir-302s share over 400 target genes with these miRNAs, suggesting that these miRNAs may also play an important role in maintaining stem cell pluripotency and renewal. These conserved target genes include, but not limited, members of RAB/RAS-related oncogenes, ECT-related oncogenes, pleiomorphic adenoma genes, E2F transcription factors, cyclin D binding Myb-like transcription factors, HMG-box transcription factors, Sp3 transcription factors, transcription factor CP2-like proteins, NFkB activating protein genes, cyclin-dependent kinases (CDKs), MAPK-related kinases, SNF-related kinases, myosin light chain kinases, TNF-alpha-induce protein genes, DAZ-associated protein genes, LIM-associated homeobox genes, DEAD/H box protein genes, forkhead box protein genes, BMP regulators, Rho/Rac guanine nucleotide exchange factors, IGF receptors, endothelin receptors, left-right determination factors, cyclins, p53 inducible nuclear protein genes, RB-like 1, RB binding protein genes, Max-binding protein genes, c-MIR cellular modulator of immune recognition, Bcl2-like apoptosis facilitator, protocadherins, integrin β4/β8, inhibin, ankyrins, SENP1, NUFIP2, FGF9/19, SMAD2, CXCR4, EIF2C, PCAF, MECP2, histone acetyltransferase MYST3, nuclear RNP H3, and many nuclear receptors and factors. All of these genes are highly involved in embryonic development and/or tumorigenicity of cancers.

Identification of ES Marker Expression Using Gene Microarray Analysis

After the co-expression correlation of ES cell markers and transgenic mir-302s is confirmed, we perform gene microarray analysis to screen the changes of genome-wide gene expression profiles in the cells before and after the mir-302 transfection as well as between the mir-302-transfected cells and other human embryonic stem (hES) cells. Affymetrix gene microarrays (GeneChip U133A&B arrays, Santa Clara, Calif.) are used to assess the changes of over 32,668 human gene expression patterns between Colo and Colo+mir-302 cells as well as between Colo+mir-302 and other hES cells, such as HuEC8 and H9. Total RNAs from each tested cell culture are isolated using RNeasy spin columns (Qiagen, Valencia, Calif.). To clearly identify the variable targets in the background, we first duplicate the microarray tests using the same Colo+mir-302 sample and select two hundred genes which are slightly presented in one side of the tests for further comparison. As shown in FIG. 8A, the changes of expression of these selected genes (white dots) are all less than one fold in the duplicated tests of Colo+mir-302, indicating that the background variation is very limited. Based on the scattering patterns of these pre-selected genes with a threshold of one-fold change, we can calculate the correlation coefficient (CC) between two compared gene transcript libraries. A CC rate is given to show the percentage of similarity of 32,668 human gene expression patterns between the compared samples. In view of such CC rates, the result of FIG. 8A demonstrates that the gene expression patterns of Colo+mir-302 cells share a very high 88% and 86% similarity to those of hES HuEC8 and H9 cells, whereas only a low 53% CC rate is presented between Colo and Colo+mir-302 cells. This suggests that the SpRNAi-RGFP-mediated mir-302 transfection changes the expression patterns of up to 15,354 cellular genes, which may be involving in the reprogramming processes of a cancerous Colo cell into an ES-like Colo+mir-302 cell.

The list of some major differentially expressed genes between Colo and Colo+mir-302 cells is shown in FIG. 8B. Like H9 and HuEC8, the Colo+mir-302 cells express high levels of many embryonic stem and germ line cell markers, such as SSEA-3, SSEA-4, Utf1, Oct4, Sox2, Pulimio-2 and Nanog. However, Klf4 is not expressed in the Colo+mir-302 cells, showing a certain difference from the iPS cells (FIG. 6B). Further, many cancer-specific markers, developmental signals and cell proliferating factors are found to be significantly down-regulated after mir-302 transfection, consistent with the observations of undifferentiated round cell morphology and slow cell replication in FIG. 5. Taken together, all these findings indicate that the use of the presently invented mir-302 transfection method can genetically reprogram and transform the differentiated Colo cell line into a highly ES-like Colo+mir-302 cell line, similar to those of the pluripotent H9 and HuEC8 stem cells.

Guidance of Cell Differentiation Using Various Hormones and Growth Factors

In definition, a pluripotent stem cell can differentiate into various cell types similar to the tissue cells derived from embryonic ectoderm, mesoderm and/or endoderm. For example, using in vitro treatments of hormones and/or growth factors under a feeder-free condition, we have successfully guided the differentiation of Colo+mir-302 cells into three different cell types as shown in FIGS. 9A-C. First, by treating Colo+mir-302 cells with a native androgen, dihydrotestosterone (DHT 50 ng/ml), for 6 hours in a feeder-free culture dish and then implanting the treated cells ($10^5$) into the uterus of a 6-week-old female immunocompromised SCID-beige mouse in vivo, a cyst of spermatogonia-like cells are generated one week later in the implantation site (FIG. 9A middle). Second, by treating Colo+mir-302 cells with transforming growth factor-beta1 (TGF-β1 100 ng/ml) for 12 hours and then implanting the treated cells into the uterus of a 6-week-old female immunocompromised SCID-beige mouse, the cells differentiate into fibroblast-like cells and start to secret collagen which occupies a large area of the uterus within just one week (FIG. 9B). Last, by treating Colo+mir-302 cells with bone morphogenetic protein 4 (BMP4 100 ng/ml) for 12 hours and then xenografting the treated cells into the liver of a 6-week-old immunocompromised SCID-beige mouse, the cells differentiate into chondrocyte-like cells surrounding with little calcified precipitates (FIG. 9C). The use of athymic nude mice is to provide an in vivo environment mimicking transplantation therapy. These findings provide strongly evidence that we have successfully used the presently invented mir-302 transfection method to generate new ES-like cell lines, which can be guided into multiple tissue cell types under a feeder-free condition in vitro. Therefore, the present invention is able not only to reprogram and transform a somatic differentiated cell into an ES-like pluripotent cell but also to maintain the pluripotent and renewal properties of a stem cell in a feeder-free cell culture condition.

Thus, utilization of intronic mir-302 expression vectors of the present invention provides a powerful new strategy for stem cell generation, particularly derived from primary somatic cell cultures and cancerous cells. Because the intronic miRNA-mediated gene silencing pathway is well coordinated by multiple intracellular regulation systems, including components of gene transcription, RNA splicing, exosome digestion and NMD processing mechanisms, the gene silencing effect of intronic miRNA is considered to be most effective, specific and safe in all three currently known RNAi pathways. Advantageously overall, the use of the presently invented intronic mir-302 agents offers a simple, effective and safe gene manipulation approach for not only reprogramming somatic cells into ES-like pluripotent cells but also maintaining ES cell pluripotent properties in a feeder-free cell culture condition, preventing the tedious retroviral insertion of four large transcription factor genes in one single cell as used in the previous iPS methods. With reference to FIG. 10, in regard to the gene expression pattern of our mir-302-induced embryonic stem (ES)-like cells, it indicates that SSEA-1 is moderately expressed in the mir-302-induced ES-like mirPS-Colo (Colo+mir-302) cells, whereas Klf4 is not.

A. Definitions

To facilitate understanding of the invention, a number of terms are defined below:

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide.

Oligonucleotide: a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Nucleic Acid: a polymer of nucleotides, either single or double stranded.

Nucleotide Analog: a purine or pyrimidine nucleotide that differs structurally from A, T, G, C, or U, but is sufficiently similar to substitute for the normal nucleotide in a nucleic acid molecule.

Nucleic Acid Composition: a nucleic acid composition refers to polynucleotides such as deoxyribonucleic acid (DNA) and ribonucleic acid (RNA) in either single-stranded or double-stranded molecular structures.

Gene: a nucleic acid whose nucleotide sequence codes for an RNA and/or a polypeptide (protein). A gene can be either RNA or DNA.

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding.

Precursor messenger RNA (pre-mRNA): primary ribonucleotide transcripts of a gene, which are produced by type-II RNA polymerase (Pol-II) machineries in eukaryotes through an intracellular mechanism termed transcription. A pre-mRNA sequence contains a 5'-end untranslated region, a 3'-end untranslated region, exons and introns.

Intron: a part or parts of a gene transcript sequence encoding non-protein-reading frames, such as in-frame intron, 5'-untranslated region (5'-UTR) and 3'-UTR.

Exon: a part or parts of a gene transcript sequence encoding protein-reading frames.

Messenger RNA (mRNA): assembly of pre-mRNA exons, which is formed after intron removal by intranuclear spliceosomal machineries and served as a protein-coding RNA for protein synthesis.

cDNA: a single stranded DNA that is complementary to an mRNA sequence and does not contain any intronic sequences.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "-" symbol or with an "a" or "antisense" in front of the DNA or RNA, e.g., "aDNA" or "aRNA".

5'-end: a terminus lacking a nucleotide at the 5' position of successive nucleotides in which the 5'-hydroxyl group of one nucleotide is joined to the 3'-hydroxyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroxyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA molecule, double stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Complementary or Complementarity or Complementation: used in reference to polynucleotides (i.e. a sequence of nucleotides) related by the base-pairing rules. For example, the sequence "A-G-T" is complementary to the sequence "T-C-A," and also to "T-C-U." Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Homologous or Homology: refers to a polynucleotide sequence having similarities with a gene or mRNA sequence. A nucleic acid sequence may be partially or completely homologous to a particular gene or mRNA sequence, for example. Homology may also be expressed as a percentage determined by the number of similar nucleotides over the total number of nucleotides.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

RNA interference (RNAi): a posttranscriptional gene silencing mechanism in eukaryotes, which can be triggered by small RNA molecules such as microRNA and small interfering RNA. These small RNA molecules usually function as gene silencers, interfering with expression of intracellular genes containing either completely or partially complementarity to the small RNAs.

MicroRNA (miRNA): single-stranded RNAs capable of binding to targeted gene transcripts that have partial complementarity to the miRNA. mRNA is usually about 17-27 oligonucleotides in length and is able to either directly degrade its intracellular mRNA target(s) or suppress the protein translation of its targeted mRNA, depending on the complementarity between the miRNA and its target mRNA. Natural miRNAs are found in almost all eukaryotes, functioning as a defense against viral infections and allowing regulation of gene expression during development of plants and animals.

Pre-miRNA: hairpin-like single-stranded RNAs containing stem-arm and stem-loop regions for interacting with intracellular RNaseIII endoribonucleases to produce one or multiple microRNAs capable of silencing a targeted gene or genes complementary to the microRNA sequence(s). The stem-arms of a pre-miRNA can form either perfectly (100%) or partially (mismatched) hybridized duplex conformation, while the stem-loop connects one end of the stem-arm duplex to form a circle or hairpin-loop conformation.

Small interfering RNA (siRNA): short double-stranded RNAs sized about 18-25 perfectly base-paired ribonucleotide duplexes and capable of degrading target gene transcripts with almost perfect complementarity.

Small or short hairpin RNA (shRNA): single-stranded RNAs that contain a pair of partially or completely matched stem-arm nucleotide sequences divided by an unmatched loop oligonucleotide to form a hairpin-like structure. Many natural miRNAs are derived from hairpin-like RNA precursors, namely precursor microRNA (pre-miRNA).

Vector: a recombinant nucleic acid molecule such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and/or expression of nucleic acids to which they are linked. Vectors capable of directing the expression of genes encoding for one or more polypeptides are referred to herein as "expression vectors". Particularly important vectors allow cloning of cDNA from mRNAs produced using a reverse transcriptase.

Cistron: a sequence of nucleotides in a DNA molecule coding for an amino acid residue sequence and including upstream and downstream DNA expression control elements.

Promoter: a nucleic acid to which a polymerase molecule recognizes, perhaps binds to, and initiates synthesis. For the purposes of the instant invention, a promoter can be a known polymerase binding site, an enhancer and the like, any sequence that can initiate synthesis by a desired polymerase.

Antibody: a peptide or protein molecule having a preselected conserved domain structure coding for a receptor capable of binding a pre-selected ligand.

B. Compositions

A recombinant nucleic acid composition for inducing intronic RNA-mediated gene silencing comprises:
  a) At least an intron, wherein said intron is flanked with a plurality of exons and can be cleaved out of the exons by intracellular RNA splicing and/or processing machineries; and
  b) A plurality of exons, wherein said exons can be linked to form a gene possessing a desired function.

The above recombinant nucleic acid composition, further comprises:
  a) At least a restriction/cloning site, wherein said restriction/cloning site is used for incorporating the recombinant nucleic acid composition into an expression-competent vector for expressing the primary RNA transcripts of said recombinant nucleic acid composition in mammalian cells; and
  b) A plurality of transcription and translation termination sites, wherein said transcription and translation termination sites are used for produce the correct sizes of the RNA transcripts of said recombinant nucleic acid composition.

The intron of the above recombinant nucleic acid composition, further comprises:
  a) A gene-silencing effector insert complementary or homologous to at least a targeted gene;
  b) A 5'-donor splice site;
  c) A 3'-acceptor splice site;
  d) A branch point motif for spliceosomal recognition;
  e) A poly-pyrimidine tract for spliceosomal interaction; and
  f) A plurality of linkers for connection of the above major components.

The gene-silencing effector insert encodes a nucleotide sequence homologous to 5'-UAAGUGCUUC CAUGUUU-3' (SEQ. ID. NO. 3). The 5'-donor splice site is a nucleotide sequence containing or homologous to either 5'-GTAAGAGK-3' (SEQ. ID. NO. 4) or GU(A/G)AGU motifs (such as 5'-GTAAGAGGAT-3' (SEQ ID NO: 30), 5'-GTAAGAGT-3', 5'-GTAGAGT-3' and 5'-GTAAGT-3'), while the 3'-acceptor splice site is a nucleotide sequence containing or homologous to either GWKSCYRCAG (SEQ. ID. NO. 5) or CT(A/G)A(C/T)NG motifs (such as 5'-GATATCCTGC AG-3'(SEQ ID NO: 31), 5'-GGCTGCAG-3' and 5'-CCACAG-3'). Moreover, a branch point sequence is located between the 5'- and 3'-splice sites, containing a motif homologous to 5'-TACTWAY-3' (SEQ. ID. NO. 6) motifs, such as 5'-TACTAAC-3' and 5'-TACTTAT-3'. Furthermore, a poly-pyrimidine tract is closely located between the branch-point and 3'-splice site, containing a high T or C content oligonucleotide sequence homologous to either 5'-(TY)m(C/-)(T)nS(C/-)-3' (SEQ. ID. NO. 7) or 5'-(TC) nNCTAG(G/-)-3' (SEQ. ID. NO. 8) motifs. The symbols of "m" and "n" indicate multiple repeats ≥1; most preferably, the m number is equal to 1~3 and the n number is equal to 7~12. The symbol "-" refers an empty nucleotide in the sequence. There are also some linker nucleotide sequences for the connection of all these intron components. Based on the guideline of 37 CFR 1.822 for symbols and format to be used for nucleotide and/or amino acid sequence data, the symbol W refers to an adenine (A) or thymine (T)/uracil (U), the symbol K refers to a guanine (G) or thymine (T)/uracil (U), the symbol S refers to a cytosine (C) or guanine (G), the symbol Y refers to a cytosine (C) or thymine (T)/uracil (U), the symbol R refers to an adenine (A) or guanine (G), and the symbol N refers to an adenine (A), cytosine (C), guanine (G) or thymine (T)/uracil (U)." For all of the above spliceosomal recognition components, the deoxythymidine (T) nucleotide is replaceable with uridine (U).

C. Methods

A transgenic method for inducing intronic mir-302-mediated gene silencing in mammalian cells comprises the steps of:
  a) Constructing a recombinant nucleic acid composition that contains at least an intron encoding a mir-302-like gene-silencing effector flanked with exons, wherein said intron can be cleaved out of the exons for executing mir-302-mediated gene silencing;

b) Cloning said recombinant nucleic acid composition into an expression-competent vector; and c) Introducing said vector into a plurality of mammalian cells, wherein said cells generate a plurality of primary RNA transcripts of said recombinant nucleic acid composition, and wherein the spliceosomes of the cells splice the intron out of the primary RNA transcripts so as to provide mir-302-mediated gene silencing effects on genes containing homology or complementarity to the sequence of the mir-302-like gene-silencing effector.

EXAMPLES

The following examples serve to illustrate certain preferred embodiments and aspects of the present invention and are not to be construed as limiting the scope thereof.

In the experimental disclosure which follows, the following abbreviations apply: M (molar); mM (millimolar); μm (micromolar); mol (moles); pmol (picomolar); gm (grams); mg (milligrams) μg (micrograms); ng (nanograms); L (liters); ml (milliliters); μl (microliters); ° C. (degrees Centigrade); cDNA (copy or complementary DNA); DNA (deoxyribonucleic acid); ssDNA (single stranded DNA); dsDNA (double-stranded DNA); dNTP (deoxyribonucleotide triphosphate); RNA (ribonucleic acid); PBS (phosphate buffered saline); NaCl (sodium chloride); HEPES (N-2-hydroxyethylpiperazine-N-2-ethanesulfonic acid); HBS (HEPES buffered saline); SDS (sodium dodecylsulfate); Tris-HCl (tris-hydroxymethylaminomethane-hydrochloride); and ATCC (American Type Culture Collection, Rockville, Md.).

Example 1

Construction of SpRNAi-Containing Recombinant Gene (SpRNAi-RGFP)

Synthetic nucleic acid sequences used for generation of three different SpRNAi introns containing either sense-, antisense- or hairpin-EGFP insert were listed as follows: N1-sense, 5'-GTAAGAGGAT CCGATCGCAG GAGCGCACCA TCTTCTTCAA GA-3' (SEQ. ID. NO. 14); N1-antisense, 5'-CGCGTCTTGA AGAAGATGGT GCGCTCCTGC GATCGGATCC TCTTAC-3' (SEQ. ID. NO. 15); N2-sense, 5'-GTAAGAGGAT CCGATCGCTT GAAGAAGATG GTGCGCTCCT GA-3' (SEQ. ID. NO. 16); N2-antisense, 5'-CGCGTCAGGA GCGCACCATC TTCTTCAAGC GATCGGATCC TCTTAC-3' (SEQ. ID. NO. 17); N3-sense, 5'-GTAAGAGGAT CCGATCGCAG GAGCGCACCA TCTTCTTCAA GTTAACTTGA AGAAGATGGT GCGCTCCTGA-3' (SEQ. ID. NO. 18); N3-antisense, 5'-CGCGTCAGGA GCGCACCATC TTCTTCAAGT TAACTTGAAG AAGATGGTGC GCTCCTGCGA TCGGATCCTC TTAC-3' (SEQ. ID. NO. 19); N4-sense, 5'-CGCGTTACTA ACTGGTACCT CTTCTTTTTT TTTTTGATAT CCTGCAG-3' (SEQ. ID. NO. 20); N4-antisense, 5'-GTCCTGCAGG ATATCAAAAA AAAAAGAAGA GGTACCAGTT AGTAA-3' (SEQ. ID. NO. 21). All sequences listed from SEQ. ID. NO. 14 to SEQ ID NO. 21 are phosphorylated in their 5'-ends. In addition, two exon fragments were generated by DraII restriction enzyme cleavage of a red fluorescent RGFP gene (SEQ. ID. NO. 22) at its 208th nucleotide (nt) site and the 5' fragment was further blunt-ended by T4 DNA polymerase. The RGFP referred to a new red-shifted fluorescent chromoprotein gene generated by insertion of an additional aspartate at the 69th amino acid (a.a.) site of HcRed1 chromoproteins from Heteractis crispa (BD Biosciences, CA), developing less aggregate and almost twice intense far-red fluorescent emission at the 570-nm wavelength. We cleaved a pHcRed1-N1/1 plasmid (BD Biosciences, CA) with XhoI and XbaI restriction enzymes and then isolated a full 769-bp RGFP gene fragment and a 3,934-bp empty plasmid, separately, by 2% agarose gel electrophoresis and extraction (gel extraction kit, Qiagen, CA).

Hybridization of N1-sense to N1-antisense, N2-sense to N2-antisense, N3-sense to N3-antisense, and N4-sense to N4-antisense was separately performed by heating each complementary mixture of sense and antisense (1:1) sequences to 94° C. for 2 min and then 70° C. for 10 min in 1×PCR buffer (e.g. 50 mM Tris-HCl, pH 9.2 at 25° C., 16 mM $(NH_4)_2SO_4$, 1.75 mM $MgCl_2$). Immediately after that, sequential ligation of either N1, N2 or N3 hybrid to the N4 hybrid was performed by gradually cooling the mixture of N1+N4, N2+N4 or N3+N4 (1:1) hybrids, respectively, from 50° C. to 10° C. over a period of 1 hr, and then $T_4$ DNA ligase and its relative 1× ligation buffer (Roche, IN) were added with the mixture for 12 hr at 12° C., so as to obtain SpRNAi introns for insertion into the break site of the DraII-cleaved RGFP exons. After the RGFP exon fragments were added into the reaction (1:1:1), T4 DNA ligase and buffer were adjusted accordingly to reiterate the ligation reaction for another 12 hr at 12° C. For cloning the right size of the recombinant SpRNAi-inserted RGFP gene, 10 ng of the ligated nucleotide sequences were amplified by PCR with a pair of RGFP-specific primers 5'-CTCGAGCATG GTGAGCGGCC TGCTGAA-3' (SEQ. ID. NO. 23) and 5'-TCTAGAAGTT GGCCTTCTCG GGCAGGT-3' (SEQ. ID. NO. 24) at 94° C., 1 min, 52°, 1 min and then 68° C., 2 min for 30 cycles. The resulting PCR products were fractionated on a 2% agarose gel, and a ~900-bp nucleotide sequences was extracted and purified using a gel extraction kit (Qiagen, CA). The composition of this ~900 bp SpRNAi-containing RGFP gene was further confirmed by sequencing. Preferably, in the absence of intronic insertion, the sense strand of the SpRNAi intron sequence is 5'-GTAAGTGGTC CGATCGTCGC GACGCGTCAT TACTAACTAT CAATATCTTA ATCCTGTCCC TTTTTTTTCC ACAGTAGGAC CTTCGTGCA-3' (SEQ. ID. NO. 25), while the antisense strand of the SpRNAi intron sequence is 5'-TGCACGAAGG TCCTACTGTG GAAAAAAAAG GGACAGGATT AAGATATTGA TAGTTAGTAA TGACGCGTCG CGACGATCGG ACCACTTAC-3' (SEQ. ID. NO. 26).

Alternatively, the recombinant SpRNAi-RGFP transgene can be made by incorporation of the SpRNAi hybrid of SEQ. ID. NO. 25 and SEQ. ID. NO. 26 into the restriction break site of the DraII-cleaved RGFP exons, and following the same protocol as shown above. The SpRNAi-RGFP transgene constructs used in the experiments of testing the manually re-designed mir-302 pre-miRNA insert (encoding SEQ. ID. NO. 9) were formed by this way.

Because the recombinant SpRNAi-RGFP gene possessed an XhoI and an XbaI restriction site at its 5'- and 3'-end, respectively, it can be easily cloned into a vector with cohesive ends to the XhoI and XbaI cloning sites. The vector must be an expressing-competent organism or suborganism selected from the group consisted of DNA transgenes, plasmids, jumping genes, transposons and viral vectors. Moreover, because the insert within the intron is also flanked with a PvuI and an MluI restriction site at its 5'- and 3'-end, respectively, we can remove and replace the intronic insert with another different insert sequence possessing cohesive ends to the PvuI and MluI cloning sites. The inserted sequence is preferably a hairpin-like gene silencing effector containing high complementarity to a gene target selected from the group consisted of fluorescent protein (GFP) genes, luciferase genes, lac-Z genes, viral genes, bacterial genes, plant genes, animal genes and human genes. The complementarity and/or homology rate between the gene-silencing effector insert and its targeted gene is ranged from about 30%-100%, more preferably 35%-49% for a hairpin-shRNA insert and 90%-100% for both sense-RNA and antisense-RNA inserts.

Example 2

Cloning of SpRNAi-Containing Genes into A Expression-Competent Vector

Because the recombinant SpRNAi-RGFP gene possessed an XhoI and an XbaI restriction site at its 5'- and 3'-end, respectively, it can be easily cloned into a vector with relatively cohesive ends to the XhoI and XbaI restriction sites. We mixed the SpRNAi-RGFP gene with the linearized 3,934-bp empty pHcRed1-N1/1 plasmid at 1:16 (w/w) ratio, cooled the mixture from 65° C. to 15° C. over a period of 50 min, and then added $T_4$ ligase and relative buffer accordingly into the mixture for ligation at 12° C. for 12 hr. This formed an SpRNAi-RGFP expression vector, which can be propagated in an E. coli DH5α LB culture containing 50 μg/ml kanamycin (Sigma Chemical, St. Louis, Mo.). A positive clone was confirmed by PCR with the RGFP-specific primers SEQ. ID. NO. 23 and SEQ. ID. NO. 24 at 94° C., 1 min and then 68° C., 2 min for 30 cycles, and for further sequencing. For cloning into viral vectors, the same ligation procedure could be performed except using an XhoI/XbaI-linearized pLNCX2 retroviral vector (BD) instead. Since the insert within the SpRNAi intron was flanked with a PvuI and a MluI restriction site at its 5'- and 3'-end, respectively, we could remove and replace the anti-EGFP shRNA insert with a re-designed mir-302 insert possessing cohesive ends to the PvuI and MluI cloning sites. The re-designed mir-302 insert sequence contains a homologous 5'-UAAGUGCUUC CAU-GUUU-3' (SEQ. ID. NO. 3) region, similar to 5'-UAAGUGCUUC CAUGUUUUAG UGU-3' (SEQ. ID. NO. 9), 5'-UAAGUGCUUC CAUGUUUUGG UGA-3' (SEQ. ID. NO. 10), 5'-UAAGUGCUUC CAUGUUUUAG UAG-3' (SEQ. ID. NO. 11), 5'-UAAGUGCUUC CAU-GUUUCAG UGG-3' (SEQ. ID. NO. 12), or 5'-UAAGUGC-UUC CAUGUUUGAG UGU-3' (SEQ. ID. NO. 13).

Synthetic nucleic acid sequences used for generation of various SpRNAi introns encoding either the mir-302 familial pre-miRNA cluster or the re-designed mir-302 insert were listed as follows: mir-302a-sense, 5'-GTCCGATCGT CCCACCACTT AAACGTGGAT GTACTTGCTT TGAAACTAAA GAAGTAAGTG CTTCCATGTTTTG-GTGATGG ATCTCGAGCT C-3' (SEQ ID NO: 39); mir-302a-antisense, 5'-GAGCTCGAGA TCCATCACCA AAACATGGAA GCACTTACTT CTTTAGTC AAAGCAAGTA CATCCACGTT TAAGTGGTGG GAC-GATCGGA C-3' (SEQ ID NO: 40); mir-302b-sense, 5'-ATCTCGAGCT CGCTCCCTTC AACTTTAACA TGGAAGTGCT TTCTGTGACT TTGAAAGTAA GTGCTTCCAT GTTTAGTAG GAGTCGCTAG CGCTA-3' (SEQ ID NO: 41); mir-302b-antisense, 5'-TAGCGGTAGC GAGTCCTACT AAAACATGGA AGCACTTACT TTCAAAGTCA CAGAAAGCAC TTC-CATGTTA AAGTTGAAGG GAGCGAGCGTC GAGAT-3' (SEQ ID NO: 42); mir-302c-sense, 5'-CGCTAGCGCT ACCTTTGCTT TAACATGGAG GTACCTGCTG TGT-GAAACAG AAGTAAGTCG TTCATGTC AGTGGAG-GCG TCTAGACAT-3' (SEQ ID NO: 43); mir-302c-antisense, 5'-ATGTCTAGAC GCCTCCACTG AAACATGAAC GACTTACTTC TGTTCACAC AGCAG-GTACC TCCATGTTAA AGCAAAGGTA GCGCTAGCG-3' (SEQ ID NO: 44); mir-302d-sense, 5'-CGTCTAGACA TAACACTCAA ACATGGAAGC ACTTAGCTAA GCCA-GGCTAA GTGCTTCCAT GTTTGAGTGT TCGACGCGTC AT-3' (SEQ ID NO: 45); mir-302d-antisense, 5'-ATGACGCGTC GAACACTCAA ACATG-GAAGC ACTTAGCCTG GCTTAGCTAA GTGCTTCCAT GTTTGAGTGT TATGTCTAGA CG-3' (SEQ ID NO: 46); and miR-302s-sense, 5'-GTCCGATCGT CATAAGTGCT TCCATGTTTT AGTGTGCTAA GCCAGGCACA CTAAAACATG GAAGCACTTA TCGACGCGTC AT-3' (SEQ. ID. NO. 27); mir-302s-antisense, 5'-ATGACGCGTC GATAAGTGCT TCCATGTTT AGTGTGCCTG GCTTAG-CACA CTAAAACATG GAAGCACTTA TGACGATCGG AC-3' (SEQ. ID. NO. 28).

The intronic insert of the mir-302 familial pre-miRNA cluster was formed by hybridization of mir-302a-sense to mir-302a-antisense, mir-302b-sense to mir-302b-antisense, mir-302c-sense to mir-302c-antisense, and mir-302d-sense to mir-302d-antisense, respectively. Then, the hybrids of mir-302a, mir-302b, mir-302c, and mir-302d were digested by PvuI/XhoI, XhoI/NheI, NheI/XbaI, and XbaI/MluI restriction enzymes, respectively, and collected together by a gel extraction filter column in 35 μl autoclaved ddH$_2$O (Qiagen, CA). Immediately after that, the collected hybrids were ligated together to form a cluster of the mir-302 familial pre-miRNA insert by T4 DNA ligase (Roche, 20 U) and used for further insertion into the PvuI/MluI-linearized SpRNAi-RGFP expression vectors. The recombinant SpRNAi-RGFP gene containing the mir-302 familial pre-miRNA cluster was inserted into a retroviral pLNCX2 vector with a pVSV-G surface antigen, which was used to transgenically infect hpESC and PC3 cells. For generating the manually re-designed mir-302 pre-miRNA insert, we hybridized two synthetic sequences of the SEQ. ID. NO. 27 and SEQ. ID. NO. 28, cleaved their hybrid with PvuI/MluI restriction enzymes, and then inserted and ligated the hybrid into the PvuI/MluI-linearized SpRNAi-RGFP expression pHcRed1 vector with T4 DNA ligase (20 U). This SpRNAi-RGFP gene containing the re-designed mir-302 pre-miRNA was directly used for transgenic DNA recombination into Colo cells. Positively transfected cells were isolated and collected 24 h later for sub-culturing, using flow cytometry selection with an anti-RGFP monoclonal antibody (Clontech, Palo Alto, Calif.).

The mir-302 pre-miRNA cluster- and mir-302s-expressing vectors so obtained could be propagated in E. coli DH5α LB-culture containing either 50 μg/ml kanamycin for the pHcRed1-N1/1 plasmid-based vector or 100 μg/ml ampicillin for the pLNCX2 retroviral vector. The propagated SpRNAi-RGFP expression vectors could be isolated and purified using a mini-prep or maxi-prep plasmid extraction kit (Qiagen, CA), following the manufacturer's suggestion. For pLNCX2 vectors, we could also use a packaging cell line GP2-293 (Clontech, CA) for producing infectious but replication-incompetent virus. The transfected GP2-293 cells were grown in 1×DMEM medium supplemented with charcoal-stripped 10% fetal bovine serum (FBS) with 4 mM L-glutamine, 1 mM sodium pyruvate, 100 μg/ml streptomycin sulfate and 50 μg/ml neomycin (Sigma Chemical, MO) at 37° C. under 5% CO$_2$. The titer of virus produced by GP2-293 cells was determined to be at least $10^6$ cfu/ml before transfection.

Example 3

In Vitro Transgenic Transfection

For retroviral vector transfection into the hpESC and PC3 cell cultures, we first cultured the SpRNAi-RGFP-expressing pLNCX2 retroviral vectors containing either an anti-EGFP mir-gfp or a mir-302 familial cluster pre-miRNA insert in the pVSV-G co-transfected GP2-293 cells (Clontech, CA). After 36-hour incubation at 37° C. under 5% $CO_2$, the cultural mediums (10 ml each) of the GP2-293 cells were filtrated (0.25 μm) and directly transferred into the hpESC and PC3 cell cultures, respectively. Since the mediums contained very high titers of the designed retroviral vectors, all the tested cells were transgenically infected by the vectors and started to express the intronic inserts and RGFP within 24 hours. For transgenic delivery of the manually re-designed mir-302 pre-miRNA into Colo cells, we first mixed the prepared SpRNAi-RGFP transgene (60 μg for 10 ml medium in each cell culture) containing the designed mir-302 pre-miRNA insert from Example 2 with a FuGene reagent (Roche, IN), following the manufacturer's suggestion. Then, the mixture was applied to the Colo cell culture for 24 hours. Since the transgene also contained a transposon-like sequence homologous to a certain non-coding region of the human genome, the positively transgenically transfected cells were selected by flow cytometry with an anti-RGFP monoclonal antibody (Clontech, CA) for further sub-culturing.

Example 4

Northern Blot Analysis

RNA (20 μg total RNA or 2 μg poly[$A^+$] RNA) was fractionated on 1% formaldehyde-agarose gels and transferred onto nylon membranes (Schleicher & Schuell, Keene, N.H.). Synthetic probes complementary to the 75-bp junction sequence flanking between the RGFP 5'-exon and the designed pre-miRNA insert were labeled with the Prime-It II kit (Stratagene, La Jolla, Calif.) by random primer extension in the presence of [$^{32}P$]-dATP (>3000 Ci/mM, Amersham International, Arlington Heights, Ill.), and purified with 10 bp-cutoff Micro Bio-Spin chromatography columns (Bio-Rad, Hercules, Calif.). Hybridization was carried out in the mixture of 50% freshly deionized formamide (pH 7.0), 5×Denhardt's solution, 0.5% SDS, 4×SSPE and 250 mg/mL denatured salmon sperm DNA fragments (18 hr, 42° C.). Membranes were sequentially washed twice in 2×SSC, 0.1% SDS (15 min, 25° C.), and once in 0.2×SSC, 0.1% SDS (45 min, 37° C.) before autoradiography.

Example 5

SDS-PAGE and Western Blot Analysis

For immunoblotting of targeted proteins, isolated cells were rinsed with ice cold PBS after growth medium was removed, and then treated with the CelLytic-M lysis/extraction reagent (Sigma, Mo.) supplemented with protease inhibitors, Leupeptin, TLCK, TAME and PMSF, following manufacture's recommendations. The cells were incubated at room temperature on a shaker for 15 min, scraped into microtubes, and centrifuged for 5 min at 12,000×g to pellet the cell debris. Protein-containing cell lysate were collected and stored at −70° C. until use. Protein determinations were measured with SOFTmax software package on an E-max microplate reader (Molecular Devices, Sunnyvale, Calif.). Each 30 μg cell lysate was added into SDS-PAGE sample buffer either with (reduced) or without (unreduced) 50 mM DTT, and boiled for 3 min before loaded onto 8% polyacylamide gels, while the reference lane was loaded with 2~3 μl molecular weight markers (Bio-Rad). SDS-polyacrylamide gel electrophoresis was performed according to the standard protocols described in Molecular Cloning, 3rd ED. Protein fractionations were electroblotted onto a nitrocellulose membrane, blocked with Odyssey blocking reagent (Li-Cor Biosciences, Lincoln, Nebr.) for 1~2 hr at the room temperature. We then assessed protein expression using primary antibodies directed against either EGFP (1:5,000; JL-8, BD), RGFP (1:10,000; BD), Oct3/4 (1:500; Santa Cruz), SSEA-3 (1:500; Santa Cruz), SSEA-4 (1:500; Santa Cruz), Sox2 (1:1000; Santa Cruz), or Klf4 (1:200; Santa Cruz) overnight at 4° C. The protein blots were then rinsed 3 times with TBS-T and exposed to a secondary antibody, goat anti-mouse IgG conjugate with Alexa Fluor 680 reactive dye (1:2,000; Molecular Probes), for 1 hr at the room temperature. After three more TBS-T rinses, scanning and image analysis were completed with Li-Cor Odyssey Infrared Imager and Odyssey Software v.10 (Li-Cor).

Example 6

Intronic RNA-Mediated Gene Silencing in Zebrafish

Tg(actin-GAL4:UAS-gfp) strain zebrafish larvae were raised in a fish container with 10 ml of 0.2× serum-free RPMI 1640 medium during transfection. A transfection pre-mix was prepared by gently dissolving 60 μl of a FuGene liposomal transfection reagent (Roche Biochemicals, Indianapolis, Ind.) in 1 ml of 1× serum-free RPMI 1640 medium. The SpRNAi-RGFP vectors (20 μg) with or without an anti-EGFP pre-miRNA insert, as described in Examples 1-2, were then mixed with the pre-mix solution, stayed on ice for 30 min and directly applied to the Tg(actin-GAL4:UAS-gfp) fish larvae in the container. Total three dosages were given in a 12 hr interval (total 60 μg). Samples were collected 60 hr after the first transfection.

Example 7

Flow Cytometry Assay

Cells were trypsinized, pelleted and fixed by re-suspending in 1 ml of pre-chilled 70% methanol in PBS for 1 hour at −20° C. The cells were pelleted and washed once with 1 ml of PBS. The cells were pelleted again and resuspended in 1 ml of 1 mg/ml propidium iodide, 0.5 mg/ml RNase in PBS for 30 min at 37° C. Approximately 15,000 cells were then analyzed on a BD FACSCalibur (San Jose, Calif.). Cell doublets were excluded by plotting pulse width versus pulse area and gating on the single cells. The collected data were analyzed using the software package Flowjo using the "Watson Pragmatic" algorithm.

Example 8

DNA Methylation Assay

We first isolated the cell genomes using a DNA isolation kit (Roche, IN). Genomic DNA samples were prepared by incubating the tested cells in 10 mM Tris-HCl (pH 8.0), 10 mM EDTA, and 0.2 mg/ml proteinase K for 3 hr at 55° C., followed by ethanol precipitation. Then, the isolated genomes were digested with a CCGG-cutting restriction enzyme HpaII (10 U), respectively, at 37° C. for 4 hours. The resulting DNA fragments were shown by 1% agarose gel electrophoresis. To determine the methylation sites in the Oct3/4 promoter region, we further treated the isolated genomic DNA with bisulfite (CpGenome DNA modification kit, Chemicon, CA) and then isolated the Oct3/4 5'-upstream promoter region using polymerase chain reaction (long template PCR extension kit, Roche, IN) with two forward primers 5'-GAGGAGTTGA GGGTACTGTG-3' (SEQ ID NO: 47) and 5'-GAGGAGCTGA GGGCACTGTG-3' (SEQ ID NO: 48) and one reverse primer 5'-GTAGAAGTGC CTCTGCCTTC C-3' (SEQ ID NO: 49). The cell genomes (100 ng) were first mixed with the primers (total 150 pmole) in 1×PCR buffer, heated to 94° C. for 4 min, and immediately cooled on ice. After that, 25 cycles of PCR were performed as follows: 92C for 1 min, 55° C. for 1 min and then 70° C. for 5 min. The resulting PCR products were collected by a PCR purification kit (Qiagen, CA) and digested with an equal mixture (5 U each) of multiple ACGT-cutting restriction enzymes, containing AclI (AACGTT), BmgBI (CACGTC), PmlI (CACGTG), SnaBI (TACGTA) and HpyCH41V (ACGT). The resulting DNA fragments so obtained were shown by 3% agarose gel electrophoresis.

Example 9

MicroRNA Microarray Analysis

Human PC3 and Colo cell lines were obtained from the American Type Culture Collection (ATCC, Rockville, Md.) and hpESC cells were prepared by trypsin-dissociated skin explants from the inventor's arm. At 70% confluency, small RNAs from each cell line were isolated, using the mirVana™ miRNA isolation kit (Ambion, Inc., Austin, Tex.) following the manufacturer's suggestion. The purity and quantity of the isolated small RNAs were assessed using 1% formaldehyde-agarose gel electrophoresis and spectrophotometer measurement (Bio-Rad, Hercules, Calif.) and then submitted to LC Sciences (San Diego, Calif.) for miRNA microarray analysis. Each microarray chip was hybridized a single sample labeled with either Cy3 or Cy5 or a pair of samples labeled with Cy3 and Cy5, respectively. Background subtraction and normalization were performed. For a dual sample assay, a p-value calculation was performed and a list of differentially expressed transcripts more than 3-fold was produced.

Example 10

Gene Microarray Analysis

To prepare labeled probes for microarray hybridization, the extracted total RNAs (2 µg) were converted into double-stranded cDNAs, using a Superscript Choice system kit (Gibco/BRL, Gaithersburg, Md.) with a modified oligo $(dT)_{24}$-T7 promoter primer, such as 5'-GGCCAGTGAA TTGTAATACG ACTCACTATA GGGAGGCGG-$(dT)_{24}$-3' (SEQ ID NO: 50), following the manufacturer's protocol. Double-stranded cDNAs were purified by phenol/chloroform extractions, precipitated with ethanol, and resuspended at a concentration of 0.5 µg/µl in diethyl pyrocarbonate (DEPC)-treated ddH$_2$O. Phase-Lock Gel (5'Prime→3'Prime, Inc., Boulder, Colo.) was used for all organic extractions to increase recovery. In-vitro transcription was performed with T7 RNA polymerase and with 1 µg of cDNA, 7.5 mM unlabeled ATP and GTP, 5 mM unlabeled UTP and CTP, and 2 mM biotin-labeled CTP and UTP (biotin-11-CTP, biotin-16-UTP, Enzo Diagnostics). Reactions were carried out for 4 hr at 37° C. and cRNA was purified by RNeasy spin columns (Qiagen, CA). A sample was separated on a 1% agarose gel to check the size range, and then µg of cRNA was fragmented randomly to an average size of 50 bases by heating at 94° C. for 35 min in 40 mM Tris-acetate, pH 8.0, 100 mM KOAc/30 mM MgOAc.

A set of four oligonucleotide microarrays (GeneChip U133A&B arrays and U133 plus 2 human genome genechips, Affymetrix, Santa Clara, Calif.) containing total over 32,668 genes were used for hybridization. Hybridizations were completed in 200 µl of AFFY buffer (Affymetrix) at 40° C. for 16 hr with constant mixing. After hybridization, arrays were rinsed three times with 200 µl of 6×SSPE-T buffer (1×0.25 M sodium chloride/15 mM sodium phosphate, pH 7.6/1 mM EDTA/0.005% Triton) and then washed with 200 µl of 6×SSPE-T for 1 hr at 50° C. The arrays were rinsed twice with 0.5×SSPE-T and washed with 0.5× SSPE-T at 50° C. for 15 min. Staining was done with 2 µg/ml streptavidin-phycoerythrin (Molecular Probes) and 1 mg/ml acetylated BSA (Sigma) in 6×SSPE-T (pH 7.6). The arrays were read at 7.5 µm with a confocal scanner (Molecular Dynamics) and analyzed with Affymetrix Microarray Suite version 4.0 software. The samples were normalized by using the total average difference between perfectly matched probe and the mismatched probe. The differential signals that were induced greater than 2-fold are collected.

Example 11

Cell Differentiation Assay

All cell lines were grown in phenol red-free DMEM with 10% charcoal-stripped fetal bovine serum (FBS). At 70% confluency, different hormones or growth factors were added into the mediums of the cell cultures, respectively, such as 50 ng/ml DHT, 100 ng/ml TGF-131, and/or 100 ng/ml BMP4. After 6 to 12 hour incubation, the cells from each treatment were trypsinized and collected in four aliquots of 200 µl 1×PBS solution, and immediately implanted into the neck skin, tail vein, uterus and liver of 6-week-old athymic immunocompromised SCID-beige nude mice in vivo.

Example 12

Statistical Analysis

Results were presented as mean±SE. Statistical analysis of data was performed by one-way ANOVA. When main effects were significant, the Dunnett's post-hoc test was used to identify the groups that differed significantly from the controls. For pairwise comparison between two treatment groups, the two-tailed student t test was used. For experiments involving more than two treatment groups, ANOVA was performed followed by a post-hoc multiple range test. Probability values of p<0.05 were considered significant. All p values were determined from two-tailed tests.

REFERENCES

The following references are hereby incorporated by reference as if fully set forth herein:
1. Thomson et al., (1998) *Science* 282: 1145-1147.
2. Takahashi and Yamanaka (2006) *Cell* 126: 663-676.
3. Okita et al., (2007) *Nature* 448: 313-317.
4. Wernig et al., (2007) *Nature* 448: 318-324.
5. Yu et al., (2007) *Science* 318: 1917-1920.

6. Meissner et al., (2006) *Nature* 439: 212-215.
7. Hanna et al., (2007) *Science* 318: 1920-1923.
8. Suh et al. (2004) *Dev. Biol.* 270: 488-498.
9. Tang et al. (2007) *Genes Dev.* 21: 644-648.
10 Murchison et al., (2007) *Genes Dev.* 21: 682-693.
11. Ghosh et al. (2000) *RNA* 6: 1325-1334.
12. Lin et al. (2004) Novel RNAi therapy—Intron-derived microRNA drugs. *Drug Design Reviews* 1: 247-255.
13. Lin et al. (2003) A novel RNA splicing-mediated gene silencing mechanism potential for genome evolution. *Biochem Biophys Res Commun.* 310: 754-760.
14. Lin et al. (2005) Asymmetry of intronic pre-microRNA structures in functional RISC assembly. *Gene* 356: 32-38.
15. Lin et al. (2006a) *Methods Mol. Biol.* 342: 295-312.
16. Lin et al. (2006b) *Methods Mol. Biol.* 342: 321-334.
17. Lin et al. (2008) *Frontiers in Bioscience* 13: 2216-2230.
18. Tang, G. (2005) *Trends Biochem Sci.* 30: 106-114.
19. Lee et al. (2003) *Nature* 425: 415-419.
20. Lewin B. (2000) *Genes*, Seventh Edition, Oxford University press, pp 688-690.
21. Scholer et al., (1989) *EMBO J.* 8: 2543-2550.
22. Rosner et al., (1990) *Nature* 345: 686-692.
23. Solter et al., (1978) *Proc. Natl. Acad. Sci. USA* 75: 5565-5569.
24. Shevinsky et al., (1982) *Cell* 30: 697-705.
25. Boyer et al., (2005) *Cell* 122: 947-956.
26. Hochedlinger et al., (2006) *Nature* 441: 1061-1067.
27. Stitzel et al., (2007) *Science* 316: 407-408.
28. O'Farrell et al., (2004) *Curr. Biol.* 14: R35-45.
29. U.S. Pat. Nos. 5,843,780, 6,200,806, 7,029,913, and 7,220,584 to Thomson.
30. U.S. Pat. Nos. 6,090,622, 6,245,566, and 6,331,406 to Gearhart.
31. U.S. Pat. No. 6,875,607 to Reubinoff.

It is understood that the examples and embodiments described herein are for illustrative purposes only and that various modifications or changes in light thereof will be suggested to persons skilled in the art, and are to be included within the spirit and purview of the invention as set forth in the appended claims. All publications and patents cited herein are incorporated herein by reference in their entirety for all purposes.

The invention claimed is:

1. A method for inducing genomic DNA demethylation and hence activating Oct3/4 and Sox2 expression in mammalian cells, comprising the steps of:
   (a) constructing a recombinant SpRNAi-RGFP nucleic acid composition that contains at least an intronic RNA gene silencing effector comprising SEQ. ID. NO. 39, SEQ. ID. NO. 40, SEQ. ID. NO. 41, SEQ. ID. NO. 42, SEQ. ID. NO. 43, SEQ. ID. NO. 44, SEQ. ID. NO. 45 and SEQ. ID. NO. 46, wherein said intronic RNA gene silencing effector is further processed into mir-302a, mir-302b, mir-302c and mir-302d in mammalian cells;
   (b) introducing said recombinant SpRNAi-RGFP nucleic acid composition into a plurality of mammalian cells, wherein said plurality of mammalian cells generate a plurality of intronic RNA gene silencing effectors; and
   (c) enabling the plurality of intronic RNA gene silencing effectors to reach a level that is sufficient to induce genomic DNA demethylation and hence activate Oct3/4 and Sox2 expression, which consequently results in reprogramming the cells into a pluripotent state.

2. The method as defined in claim 1, wherein said mammalian cells are human cells.

3. The method as defined in claim 1, wherein said mammalian cells are somatic cells.

4. The method as defined in claim 1, wherein said mammalian cells are cancerous cells.

5. The method as defined in claim 1, further comprising a step of synthesizing nucleic acid components of said nucleic acid composition.

6. The method as defined in claim 1, wherein said recombinant SpRNAi-RGFP nucleic acid composition contains a recombinant cellular gene.

7. The method as defined in claim 1, wherein said recombinant SpRNAi-RGFP nucleic acid composition contains a marker protein gene.

8. The method as defined in claim 1, wherein said nucleic acid composition is constructed by a genetic engineering method.

9. The method as defined in claim 1, wherein said recombinant SpRNAi-RGFP nucleic acid composition is a nucleic acid sequence containing components of an intronic insert encoding an intronic RNA gene silencing effector, a branch point motif, a poly-pyrimidine tract, a donor splice site and an acceptor splice site.

10. The method as defined in claim 9, wherein said intronic insert is a hairpin-like nucleic acid sequence containing a stem-loop structure homologous to either SEQ. ID. NO. 1 or SEQ. ID. NO. 2.

11. The method as defined in claim 9, wherein said intronic insert is a nucleic acid sequence containing either homology or complementarity, or both, to SEQ. ID. NO. 3.

12. The method as defined in claim 9, wherein the intronic insert is incorporated into said recombinant intron through at least a restriction/cloning site.

13. The method as defined in claim 9, wherein said branch point is an adenosine (A) nucleotide located within a nucleic acid sequence containing or homologous to the SEQ. ID. NO. 6 sequence.

14. The method as defined in claim 9, wherein said poly-pyrimidine tract is a high T or C content nucleic acid sequence containing or homologous to the SEQ. ID. NO. 7 sequence.

15. The method as defined in claim 9, wherein said donor splice site is a nucleic acid sequence either containing or homologous to the SEQ. ID. NO. 4 sequence.

16. The method as defined in claim 9, wherein said acceptor splice site is a nucleic acid sequence either containing or homologous to the SEQ. ID. NO. 5 sequence.

17. The method as defined in claim 1, wherein said recombinant SpRNAi-RGFP nucleic acid composition is a plasmid.

18. The method as defined in claim 1, wherein said recombinant SpRNAi-RGFP nucleic acid composition contains a viral or type-II RNA polymerase (Pol-II) promoter or both, a Kozak consensus translation initiation site, polyadenylation signals and a plurality of restriction/cloning sites.

19. The method as defined in claim 18, wherein said restriction/cloning site is an oligonucleotide cleavage domain for an endonuclease.

20. The method as defined in claim 18, wherein said recombinant SpRNAi-RGFP nucleic acid composition further contains a pUC origin of replication, a SV40 early promoter for expressing at least an antibiotic resistance gene in replication-competent prokaryotic cells and an optional SV40 origin for replication in mammalian cells.

21. The method as defined in claim 1, wherein said recombinant SpRNAi-RGFP nucleic acid composition is introduced into said mammalian cells by a gene delivery method.

22. The method as defined in claim 1, wherein the primary RNA transcript of said recombinant SpRNAi-RGFP nucleic acid composition is generated by transcription machinery selected from the group consisting of type-II (Pol-II) and Pol-II-like RNA polymerase transcription machineries.

23. The method as defined in claim 1, wherein the primary RNA transcript of said recombinant SpRNAi-RGFP nucleic acid composition contains a microRNA.

24. The method as defined in claim 1, wherein said intronic RNA gene silencing effector is released from said recombinant intron by an intron excision mechanism selected from the group consisting of RNA splicing, exosome digestion, nonsense-mediated decay (NMD) processing, and a combination thereof.

25. The method as defined in claim 1, wherein said intronic RNA gene silencing effector has an effect on intracellular posttranscriptional gene silencing, translational suppression, RNA interference, and/or nonsense-mediated decay mechanism.

26. The method as defined in claim 1, wherein said pluripotent cells express mir-302 microRNAs.

27. The method as defined in claim 1, wherein cells in said pluripotent state express embryonic stem cell markers Oct3/4, SSEA-3, and SSEA-4.

28. The method as defined in claim 1, wherein cells in said pluripotent state can be cultured under DMEM with 10% charcoal-stripped FBS.

29. The method as defined in claim 1, wherein cells in said pluripotent state can differentiate into somatic cells.

30. The method as defined in claim 1, wherein cells in said pluripotent state can form embryoid body-like colonies.

31. The method as defined in claim 1, wherein said intronic RNA gene silencing effector shares some homologous target genes with mir-302 familial members.

32. The method as defined in claim 1, wherein cells in said pluripotent state can be selectively isolated using mir-302 microRNAs and Oct3/4 as markers.

* * * * *

```
SEQUENCE LISTING

<160> NUMBER OF SEQ ID NOS: 50

<210> SEQ ID NO 1
<211> LENGTH: 12
<212> TYPE: DNA
<213> ORGANISM: Artificial Sequence
<220> FEATURE:
<223> OTHER INFORMATION: Chemically synthesized oligonucleotide

<400> SEQUENCE: 1
gctaagccag gc                                                         12

<210> SEQ ID NO 2
<211> LENGTH: 12
<212> TYPE: DNA
<213> ORGANISM: Artificial Sequence
<220> FEATURE:
<223> OTHER INFORMATION: Chemically synthesized oligonucleotide

<400> SEQUENCE: 2
gcctggctta gc                                                         12

<210> SEQ ID NO 3
<211> LENGTH: 17
<212> TYPE: RNA
<213> ORGANISM: Artificial Sequence
<220> FEATURE:
<223> OTHER INFORMATION: Chemically synthesized oligonucleotide

<400> SEQUENCE: 3
uaagugcuuc cauguuu                                                    17

<210> SEQ ID NO 4
<211> LENGTH: 8
<212> TYPE: DNA
<213> ORGANISM: Artificial Sequence
<220> FEATURE:
<223> OTHER INFORMATION: Chemically synthesized oligonucleotide

<400> SEQUENCE: 4 gtaagagk                                                               8

<210> SEQ ID NO 5
```

```
<211> LENGTH: 10
<212> TYPE: DNA
<213> ORGANISM: Artificial Sequence
<220> FEATURE:
<223> OTHER INFORMATION: Chemically synthesized oligonucleotide

<400> SEQUENCE: 5 gwkscyrcag                                                          10

<210> SEQ ID NO 6
<211> LENGTH: 7
<212> TYPE: DNA
<213> ORGANISM: Artificial Sequence
<220> FEATURE:
<223> OTHER INFORMATION: Chemically synthesized oligonucleotide

<400> SEQUENCE: 6 tactway                                                             7

<210> SEQ ID NO 7
<211> LENGTH: 17
<212> TYPE: DNA
<213> ORGANISM: Artificial Sequence
<220> FEATURE:
<223> OTHER INFORMATION: Chemically synthesized oligonucleotide

<400> SEQUENCE: 7
tytycttttt tttttts                                                  17

<210> SEQ ID NO 8
<211> LENGTH: 19
<212> TYPE: DNA
<213> ORGANISM: Artificial Sequence
<220> FEATURE:
<223> OTHER INFORMATION: Chemically synthesized oligonucleotide
<220> FEATURE:
<221> NAME/KEY: misc_feature
<222> LOCATION: (15)..(15)
<223> OTHER INFORMATION: n is a, c, g, or t

<400> SEQUENCE: 8
tctctctctc tctcnctag                                                19

<210> SEQ ID NO 9
<211> LENGTH: 23
<212> TYPE: RNA
<213> ORGANISM: Artificial Sequence
<220> FEATURE:
<223> OTHER INFORMATION: Chemically synthesized oligonucleotide

<400> SEQUENCE: 9
uaagugcuuc cauguuuuag ugu                                           23

<210> SEQ ID NO 10
<211> LENGTH: 23
<212> TYPE: RNA
<213> ORGANISM: Artificial Sequence
<220> FEATURE:
<223> OTHER INFORMATION: Chemically synthesized oligonucleotide

<400> SEQUENCE: 10
uaagugcuuc cauguuuugg uga                                           23

<210> SEQ ID NO 11
<211> LENGTH: 23
<212> TYPE: RNA
<213> ORGANISM: Artificial Sequence
```

-continued

```
<220> FEATURE:
<223> OTHER INFORMATION: Chemically synthesized oligonucleotide

<400> SEQUENCE: 11
uaagugcuuc cauguuuag uag                                              23

<210> SEQ ID NO 12
<211> LENGTH: 23
<212> TYPE: RNA
<213> ORGANISM: Artificial Sequence
<220> FEATURE:
<223> OTHER INFORMATION: Chemically synthesized oligonucleotide

<400> SEQUENCE: 12
uaagugcuuc cauguuucag ugg                                             23

<210> SEQ ID NO 13
<211> LENGTH: 23
<212> TYPE: RNA
<213> ORGANISM: Artificial Sequence
<220> FEATURE:
<223> OTHER INFORMATION: Chemically synthesized oligonucleotide

<400> SEQUENCE: 13
uaagugcuuc cauguuugag ugu                                             23

<210> SEQ ID NO 14
<211> LENGTH: 42
<212> TYPE: DNA
<213> ORGANISM: Artificial Sequence
<220> FEATURE:
<223> OTHER INFORMATION: Chemically synthesized oligonucleotide

<400> SEQUENCE: 14
gtaagaggat ccgatcgcag gagcgcacca tcttcttcaa ga                        42

<210> SEQ ID NO 15
<211> LENGTH: 46
<212> TYPE: DNA
<213> ORGANISM: Artificial Sequence
<220> FEATURE:
<223> OTHER INFORMATION: Chemically synthesized oligonucleotide

<400> SEQUENCE: 15
cgcgtcttga agaagatggt gcgctcctgc gatcggatcc tcttac                    46

<210> SEQ ID NO 16
<211> LENGTH: 42
<212> TYPE: DNA
<213> ORGANISM: Artificial Sequence
<220> FEATURE:
<223> OTHER INFORMATION: Chemically synthesized oligonucleotide

<400> SEQUENCE: 16
gtaagaggat ccgatcgctt gaagaagatg gtgcgctcct ga                        42

<210> SEQ ID NO 17
<211> LENGTH: 46
<212> TYPE: DNA
<213> ORGANISM: Artificial Sequence
<220> FEATURE:
<223> OTHER INFORMATION: Chemically synthesized oligonucleotide

<400> SEQUENCE: 17
cgcgtcagga gcgcaccatc ttcttcaagc gatcggatcc tcttac                    46
```

<210> SEQ ID NO 18
<211> LENGTH: 70
<212> TYPE: DNA
<213> ORGANISM: Artificial Sequence
<220> FEATURE:
<223> OTHER INFORMATION: Chemically synthesized oligonucleotide

<400> SEQUENCE: 18
gtaagaggat ccgatcgcag gagcgcacca tcttcttcaa gttaacttga agaagatggt    60
gcgctcctga                                                          70

<210> SEQ ID NO 19
<211> LENGTH: 74
<212> TYPE: DNA
<213> ORGANISM: Artificial Sequence
<220> FEATURE:
<223> OTHER INFORMATION: Chemically synthesized oligonucleotide

<400> SEQUENCE: 19
cgcgtcagga gcgcaccatc ttcttcaagt taacttgaag aagatggtgc gctcctgcga    60
tcggatcctc ttac                                                     74

<210> SEQ ID NO 20
<211> LENGTH: 47
<212> TYPE: DNA
<213> ORGANISM: Artificial Sequence
<220> FEATURE:
<223> OTHER INFORMATION: Chemically synthesized oligonucleotide

<400> SEQUENCE: 20
cgcgttacta actggtacct cttcttttt tttttgatat cctgcag                  47

<210> SEQ ID NO 21
<211> LENGTH: 45
<212> TYPE: DNA
<213> ORGANISM: Artificial Sequence
<220> FEATURE:
<223> OTHER INFORMATION: Chemically synthesized oligonucleotide

<400> SEQUENCE: 21
gtcctgcagg atatcaaaaa aaaaagaaga ggtaccagtt agtaa                   45

<210> SEQ ID NO 22
<211> LENGTH: 689
<212> TYPE: DNA
<213> ORGANISM: Artificial Sequence
<220> FEATURE:
<223> OTHER INFORMATION: Mutated red fluorescent protein gene by adding
      an aspartate (Asp) codon at the 69th amino acid of a HcRed1
      chromoprotein gene from Heteractis crispa

<400> SEQUENCE: 22
atggtgagcg gcctgctgaa ggagagtatg cgcatcaaga tgtacatgga gggcaccgtg    60
aacggccact acttcaagtg cgagggcgag ggcgacggca cccccttcgc cggcacccag   120
agcatgagaa tccacgtgac cgagggcgcc cccctgccct tcgccttcga catcctggcc   180
ccctgctgcg agtacggcag caggacgacc ttcgtgcacc acaccgccga tcccccgac   240 ttcttcaagc agagcttccc cgagggcttc acctgggaga gaaccaccac ctacgaggac   300
ggcggcatcc tgaccgccca ccaggacacc agcctggagg gcaactgcct gatctacaag   360
gtgaaggtgc acggcaccaa cttccccgcc gacggcccg tgatgaagaa caagagcggc   420
ggctgggagc ccagcaccga ggtggtgtac cccgagaacg gcgtgctgtg cggccggaac   480

```
gtgatggccc tgaaggtggg cgaccggcac ctgatctgcc accactacac cagctaccgg    540
agcaagaagg ccgtgcgcgc cctgaccatg cccggcttcc acttcaccga catccggctc    600
cagatgctgc ggaagaagaa ggacgagtac ttcgagctgt acgaggccag cgtggcccgg    660
tacagcgacc tgcccgagaa ggccaactg                                      689
```

```
<210> SEQ ID NO 23
<211> LENGTH: 27
<212> TYPE: DNA
<213> ORGANISM: Artificial Sequence
<220> FEATURE:
<223> OTHER INFORMATION: Chemically synthesized oligonucleotide

<400> SEQUENCE: 23
ctcgagcatg gtgagcggcc tgctgaa                                         27
```

```
<210> SEQ ID NO 24
<211> LENGTH: 27
<212> TYPE: DNA
<213> ORGANISM: Artificial Sequence
<220> FEATURE:
<223> OTHER INFORMATION: Chemically synthesized oligonucleotide

<400> SEQUENCE: 24
tctagaagtt ggccttctcg ggcaggt                                         27
```

```
<210> SEQ ID NO 25
<211> LENGTH: 89
<212> TYPE: DNA
<213> ORGANISM: Artificial Sequence
<220> FEATURE:
<223> OTHER INFORMATION: Chemically synthesized oligonucleotide

<400> SEQUENCE: 25
gtaagtggtc cgatcgtcgc gacgcgtcat tactaactat caatatctta atcctgtccc    60
ttttttttcc acagtaggac cttcgtgca                                       89
```

```
<210> SEQ ID NO 26
<211> LENGTH: 89
<212> TYPE: DNA
<213> ORGANISM: Artificial Sequence
<220> FEATURE:
<223> OTHER INFORMATION: Chemically synthesized oligonucleotide

<400> SEQUENCE: 26
tgcacgaagg tcctactgtg gaaaaaaaag gacaggatt aagatattga tagttagtaa    60
tgacgcgtcg cgacgatcgg accacttac                                       89
```

```
<210> SEQ ID NO 27
<211> LENGTH: 82
<212> TYPE: DNA
<213> ORGANISM: Artificial Sequence
<220> FEATURE:
<223> OTHER INFORMATION: Chemically synthesized oligonucleotide

<400> SEQUENCE: 27
gtccgatcgt cataagtgct tccatgtttt agtgtgctaa gccaggcaca ctaaaacatg    60
gaagcactta tcgacgcgtc at                                              82
```

```
<210> SEQ ID NO 28
<211> LENGTH: 82
<212> TYPE: DNA
```

<210> SEQ ID NO 28
<211> LENGTH: 82
<212> TYPE: DNA
<213> ORGANISM: Artificial Sequence
<220> FEATURE:
<223> OTHER INFORMATION: Chemically synthesized oligonucleotide

<400> SEQUENCE: 28
atgacgcgtc gataagtgct tccatgtttt agtgtgcctg gcttagcaca ctaaaacatg    60
gaagcactta tgacgatcgg ac                                            82

<210> SEQ ID NO 29
<211> LENGTH: 11
<212> TYPE: RNA
<213> ORGANISM: Artificial Sequence
<220> FEATURE:
<223> OTHER INFORMATION: Chemically synthesized oligonucleotide

<400> SEQUENCE: 29
wuccaagggg g                                                        11

<210> SEQ ID NO 30
<211> LENGTH: 10
<212> TYPE: DNA
<213> ORGANISM: Artificial Sequence
<220> FEATURE:
<223> OTHER INFORMATION: Chemically synthesized oligonucleotide

<400> SEQUENCE: 30
gtaagaggat                                                          10

<210> SEQ ID NO 31
<211> LENGTH: 12
<212> TYPE: DNA
<213> ORGANISM: Artificial Sequence
<220> FEATURE:
<223> OTHER INFORMATION: Chemically synthesized oligonucleotide

<400> SEQUENCE: 31
gatatcctgc ag                                                       12

<210> SEQ ID NO 32
<211> LENGTH: 65
<212> TYPE: DNA
<213> ORGANISM: Artificial Sequence
<220> FEATURE:
<223> OTHER INFORMATION: Chemically synthesized oligonucleotide

<400> SEQUENCE: 32
aggtaagagt cgatcgacgc gttactaact ggtacctctt cttttttttt tgatatcctg    60
caggc                                                               65

<210> SEQ ID NO 33
<211> LENGTH: 53
<212> TYPE: DNA
<213> ORGANISM: Artificial Sequence
<220> FEATURE:
<223> OTHER INFORMATION: Chemically synthesized oligonucleotide

<400> SEQUENCE: 33
aagaagatgg tgcgctcctg gatcaagaga ttccaggagc gcaccatctt ctt           53

<210> SEQ ID NO 34
<211> LENGTH: 54
<212> TYPE: DNA
<213> ORGANISM: Artificial Sequence
<220> FEATURE:
<223> OTHER INFORMATION: Chemically synthesized oligonucleotide

```
<400> SEQUENCE: 34
caagaagatg gtgcgctcct ggatcaagag attccaggag cgcaccatct tctt          54

<210> SEQ ID NO 35
<211> LENGTH: 53
<212> TYPE: DNA
<213> ORGANISM: Artificial Sequence
<220> FEATURE:
<223> OTHER INFORMATION: Chemically synthesized oligonucleotide

<400> SEQUENCE: 35
aagaagatgg tgcgctcctg gatcaagaga ttccaggagc gcaccatctt ctt           53

<210> SEQ ID NO 36
<211> LENGTH: 25
<212> TYPE: DNA
<213> ORGANISM: Artificial Sequence
<220> FEATURE:
<223> OTHER INFORMATION: Chemically synthesized oligonucleotide

<400> SEQUENCE: 36
gttgttttgt tttggttttg gatat                                          25

<210> SEQ ID NO 37
<211> LENGTH: 26
<212> TYPE: DNA
<213> ORGANISM: Artificial Sequence
<220> FEATURE:
<223> OTHER INFORMATION: Chemically synthesized oligonucleotide

<400> SEQUENCE: 37
attgttttgt tttggttttg gattta                                         26

<210> SEQ ID NO 38
<211> LENGTH: 21
<212> TYPE: DNA
<213> ORGANISM: Artificial Sequence
<220> FEATURE:
<223> OTHER INFORMATION: Chemically synthesized oligonucleotide

<400> SEQUENCE: 38
gtagaagtgc ctctgccttc c                                              21

<210> SEQ ID NO 39
<211> LENGTH: 91
<212> TYPE: DNA
<213> ORGANISM: Artificial Sequence
<220> FEATURE:
<223> OTHER INFORMATION: Chemically synthesized oligonucleotide

<400> SEQUENCE: 39
gtccgatcgt cccaccactt aaacgtggat gtacttgctt tgaaactaaa gaagtaagtg    60
cttccatgtt tggtgatgg atctcgagct c                                    91

<210> SEQ ID NO 40
<211> LENGTH: 91
<212> TYPE: DNA
<213> ORGANISM: Artificial Sequence
<220> FEATURE:
<223> OTHER INFORMATION: Chemically synthesized oligonucleotide

<400> SEQUENCE: 40
gagctcgaga tccatcacca aacatggaa gcacttactt ctttagtttc aaagcaagta     60
```
catccacgtt taagtggtgg gacgatcgga c    91

<210> SEQ ID NO 41
<211> LENGTH: 95
<212> TYPE: DNA
<213> ORGANISM: Artificial Sequence
<220> FEATURE:
<223> OTHER INFORMATION: Chemically synthesized oligonucleotide

<400> SEQUENCE: 41
atctcgagct cgctcccttc aactttaaca tggaagtgct ttctgtgact ttgaaagtaa    60
gtgcttccat gttttagtag gagtcgctag cgcta    95

<210> SEQ ID NO 42
<211> LENGTH: 95
<212> TYPE: DNA
<213> ORGANISM: Artificial Sequence
<220> FEATURE:
<223> OTHER INFORMATION: Chemically synthesized oligonucleotide

<400> SEQUENCE: 42
tagcgctagc gactcctact aaaacatgga agcacttact ttcaaagtca cagaaagcac    60
ttccatgtta aagttgaagg gagcgagctc gagat    95

<210> SEQ ID NO 43
<211> LENGTH: 89
<212> TYPE: DNA
<213> ORGANISM: Artificial Sequence
<220> FEATURE:
<223> OTHER INFORMATION: Chemically synthesized oligonucleotide

<400> SEQUENCE: 43
cgctagcgct acctttgctt taacatggag gtacctgctg tgtgaaacag aagtaagtcg    60
ttcatgtttc agtggaggcg tctagacat    89

<210> SEQ ID NO 44
<211> LENGTH: 89
<212> TYPE: DNA
<213> ORGANISM: Artificial Sequence
<220> FEATURE:
<223> OTHER INFORMATION: Chemically synthesized oligonucleotide

<400> SEQUENCE: 44
atgtctagac gcctccactg aaacatgaac gacttacttc tgtttcacac agcaggtacc    60
tccatgttaa agcaaaggta gcgctagcg    89

<210> SEQ ID NO 45
<211> LENGTH: 82
<212> TYPE: DNA
<213> ORGANISM: Artificial Sequence
<220> FEATURE:
<223> OTHER INFORMATION: Chemically synthesized oligonucleotide

<400> SEQUENCE: 45
cgtctagaca taacactcaa acatggaagc acttagctaa gccaggctaa gtgcttccat    60
gtttgagtgt tcgacgcgtc at    82

<210> SEQ ID NO 46
<211> LENGTH: 82
<212> TYPE: DNA
<213> ORGANISM: Artificial Sequence
<220> FEATURE:
<223> OTHER INFORMATION: Chemically synthesized oligonucleotide

```
<400> SEQUENCE: 46
atgacgcgtc gaacactcaa acatggaagc acttagcctg gcttagctaa gtgcttccat        60
gtttgagtgt tatgtctaga cg                                                 82

<210> SEQ ID NO 47
<211> LENGTH: 20
<212> TYPE: DNA
<213> ORGANISM: Artificial Sequence
<220> FEATURE:
<223> OTHER INFORMATION: Chemically synthesized oligonucleotide

<400> SEQUENCE: 47
gaggagttga gggtactgtg                                                    20

<210> SEQ ID NO 48
<211> LENGTH: 20
<212> TYPE: DNA
<213> ORGANISM: Artificial Sequence
<220> FEATURE:
<223> OTHER INFORMATION: Chemically synthesized oligonucleotide

<400> SEQUENCE: 48
gaggagctga gggcactgtg                                                    20

<210> SEQ ID NO 49
<211> LENGTH: 21
<212> TYPE: DNA
<213> ORGANISM: Artificial Sequence
<220> FEATURE:
<223> OTHER INFORMATION: Chemically synthesized oligonucleotide

<400> SEQUENCE: 49
gtagaagtgc ctctgccttc c                                                  21

<210> SEQ ID NO 50
<211> LENGTH: 63
<212> TYPE: DNA
<213> ORGANISM: Artificial Sequence
<220> FEATURE:
<223> OTHER INFORMATION: Chemically synthesized oligonucleotide

<400> SEQUENCE: 50
ggccagtgaa ttgtaatacg actcactata gggaggcggt tttttttttt tttttttttt        60
ttt                                                                      63
```